(12) United States Patent
Fischer et al.

(10) Patent No.: US 10,939,875 B2
(45) Date of Patent: Mar. 9, 2021

(54) OPTIMIZED REAL PEAK DETECTION IN CYCLIC BIOLOGICAL DATA SIGNALS

(71) Applicant: FUJITSU LIMITED, Kawasaki (JP)

(72) Inventors: Jeffrey N. Fischer, Sunnyvale, CA (US); Ajay Chander, San Francisco, CA (US)

(73) Assignee: FUJITSU LIMITED, Kawasaki (JP)

( * ) Notice: Subject to any disclaimer, the term of this patent is extended or adjusted under 35 U.S.C. 154(b) by 463 days.

(21) Appl. No.: 15/881,592

(22) Filed: Jan. 26, 2018

(65) Prior Publication Data
US 2019/0231277 A1    Aug. 1, 2019

(51) Int. Cl.
*A61B 5/00*   (2006.01)
*G16H 10/60*  (2018.01)
(Continued)

(52) U.S. Cl.
CPC ........ *A61B 5/7278* (2013.01); *A61B 5/02405* (2013.01); *A61B 5/02416* (2013.01);
(Continued)

(58) Field of Classification Search
CPC ..... A61B 5/7278; A61B 5/7203; A61B 5/725; A61B 5/7225; A61B 8/565;
(Continued)

(56) References Cited

U.S. PATENT DOCUMENTS 3,552,386 A    1/1971 Horth
5,666,959 A    9/1997 Deans et al.
(Continued)

FOREIGN PATENT DOCUMENTS

EP    1230893 A2    8/2002
EP    2346399 A1    7/2011
(Continued)

OTHER PUBLICATIONS

Pan and Tompkins, "A Real-Time QRS Detection Algorithm", IEEE Trans. On Biodmedical Engineering, Mar. 1985.
(Continued)

*Primary Examiner* — Eric F Winakur
*Assistant Examiner* — Abid A Mustansir
(74) *Attorney, Agent, or Firm* — Maschoff Brennan

(57) ABSTRACT

A method of real peak detection includes optimizing a scoring function using training signals with known peaks and known features. The method includes receiving an input signal measured from a mobile sensor and representative of a cyclic biological process. The method includes filtering the input signal to remove low and high frequency noise. The method includes identifying candidate peaks and troughs within a selected time range of the input signal. The method includes extracting a feature that describes properties of the two or more candidate peaks. The method includes scoring the candidate peaks using the scoring function, selecting a real peak as the candidate peak with the highest score, and generating a biologic interval data set with the real peak and another peak that is representative of health markers. The method includes assessing a condition of the patient based on the biologic interval data set.

20 Claims, 14 Drawing Sheets

(51) Int. Cl.
 *A61B 8/00* (2006.01)
 *A61B 5/024* (2006.01)
 *A61B 8/02* (2006.01)
 *A61B 8/08* (2006.01)
 *G06N 20/00* (2019.01)

(52) U.S. Cl.
 CPC ............ *A61B 5/7203* (2013.01); *A61B 5/725* (2013.01); *A61B 5/7225* (2013.01); *A61B 5/7267* (2013.01); *A61B 8/02* (2013.01); *A61B 8/5223* (2013.01); *A61B 8/5269* (2013.01); *A61B 8/565* (2013.01); *G06N 20/00* (2019.01); *G16H 10/60* (2018.01)

(58) Field of Classification Search
 CPC ... A61B 5/02405; A61B 5/02416; A61B 8/02; A61B 8/5269; A61B 8/5223; A61B 5/7267; A61B 5/0245; A61B 5/0472; A61B 5/1135; G06N 20/00; G16H 10/60; G16H 50/30
 See application file for complete search history.

(56) References Cited

U.S. PATENT DOCUMENTS

| | | | |
|---|---|---|---|
| 6,029,087 | A | 2/2000 | Wohlgemuth |
| 6,937,888 | B2 | 8/2005 | Köhler et al. |
| 7,206,630 | B1 | 4/2007 | Tarler |
| 8,050,751 | B2 | 11/2011 | Zhang et al. |
| 8,380,285 | B2 | 2/2013 | Frank et al. |
| 8,679,027 | B2 | 3/2014 | Addison et al. |
| 8,768,440 | B1 | 7/2014 | Brodnick et al. |
| 8,788,024 | B1 | 7/2014 | Brodnick et al. |
| 8,812,091 | B1 | 8/2014 | Brodnick |
| 8,849,388 | B2 | 9/2014 | Brodnick et al. |
| 9,014,794 | B2 | 4/2015 | Brodnick et al. |
| 9,078,575 | B2 | 7/2015 | Brodnick |
| 9,132,274 | B2 | 9/2015 | Ghosh |
| 9,572,505 | B2 | 2/2017 | Ghosh et al. |
| 2004/0097814 | A1* | 5/2004 | Navakatikyan ...... G06K 9/0053 600/485 |
| 2016/0360974 | A1* | 12/2016 | Lange ................. A61B 5/0006 |

FOREIGN PATENT DOCUMENTS

| | | |
|---|---|---|
| EP | 2906113 A | 8/2015 |
| WO | WO/2010/014063 A1 | 2/2010 |
| WO | WO/2014/058664 A1 | 4/2014 |
| WO | WO/2016/201130 A1 | 6/2016 |
| WO | WO/2017/023393 A1 | 5/2017 |

OTHER PUBLICATIONS

Friesen, et al., "A Comparison of the Noise Sensitivity of Nine QRS Peak Detection Algorithms", IEEE Trans. On Biomedical Engineering, Jan. 1990.

Zong et al., "An Open-source Algorithm to Detect Onset of Arterial Blood Pressure Pulses", Computers in Cardiology, 30:259-262, Sep. 21, 2003.

Martinez, et al., "A Wavelet-Based ECG Delineator: Evaluation on Standard Databases", IEEE Transaction on Biomedical Engineering, Apr. 2004.

* cited by examiner

500C

500D

US 10,939,875 B2

OPTIMIZED REAL PEAK DETECTION IN CYCLIC BIOLOGICAL DATA SIGNALS

FIELD

The embodiments discussed herein are related to optimized real peak detection in cyclic biological data signals.

BACKGROUND

Heartbeat intervals and other biological data intervals are useful in medical, fitness, and wellness applications. For example, heartbeat intervals may be used to determine a heart rate of an individual and a heart rate variability of the individual. In some systems, the heartbeat intervals may be captured from a cyclic signal that corresponds to heart activity. The heartbeat interval may correspond to time distances between peaks in the cyclic signal.

Determination of the heartbeat intervals rely on detection of peaks in the cyclic signals. In some systems, the peaks in the cyclic signal may not be accurately detected. Alternatively, the peaks may be detected, but one or more other features of the cyclic signal, which may correspond to physiological conditions of the user, may be obscured or removed during processing of the cyclic signal.

The subject matter claimed herein is not limited to embodiments that solve any disadvantages or that operate only in environments such as those described. Rather, this background is only provided to illustrate one example technology area where some embodiments described herein may be practiced.

SUMMARY

According to an aspect of an embodiment, a method of peak detection in digital signals derived from a cyclic biological process may include optimizing a scoring function. The method may include receiving an input signal using training signals that include one or more known peaks and one or more known features. The input signal may include a digital signal derived from a cyclic biological process that may be measured from a mobile sensor. The method may include filtering, using a bandpass filter, and the input signal to remove low frequency noise and high frequency noise. The method may include selecting a time range of the input signal based on underlying physiological properties of a source. The method may include identifying two or more candidate peaks and two or more troughs within the selected time range. The method may include extracting a feature that describes properties of the two or more candidate peaks. The method may include scoring the two or more candidate peaks using the scoring function. The method may include selecting a real peak from the two or more candidate peaks as the candidate peak with the highest score calculated according to the scoring function. The method may include generating a biologic interval data set that includes the real peak and at least one other peak. The biologic interval data set being representative of health markers related to a condition of the patient. The method may include based on the biologic interval data set, assessing the condition of the patient.

The object and advantages of the embodiments will be realized and achieved at least by the elements, features, and combinations particularly pointed out in the claims. It is to be understood that both the foregoing general description and the following detailed description are exemplary and explanatory and are not restrictive of the present disclosure, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1A:
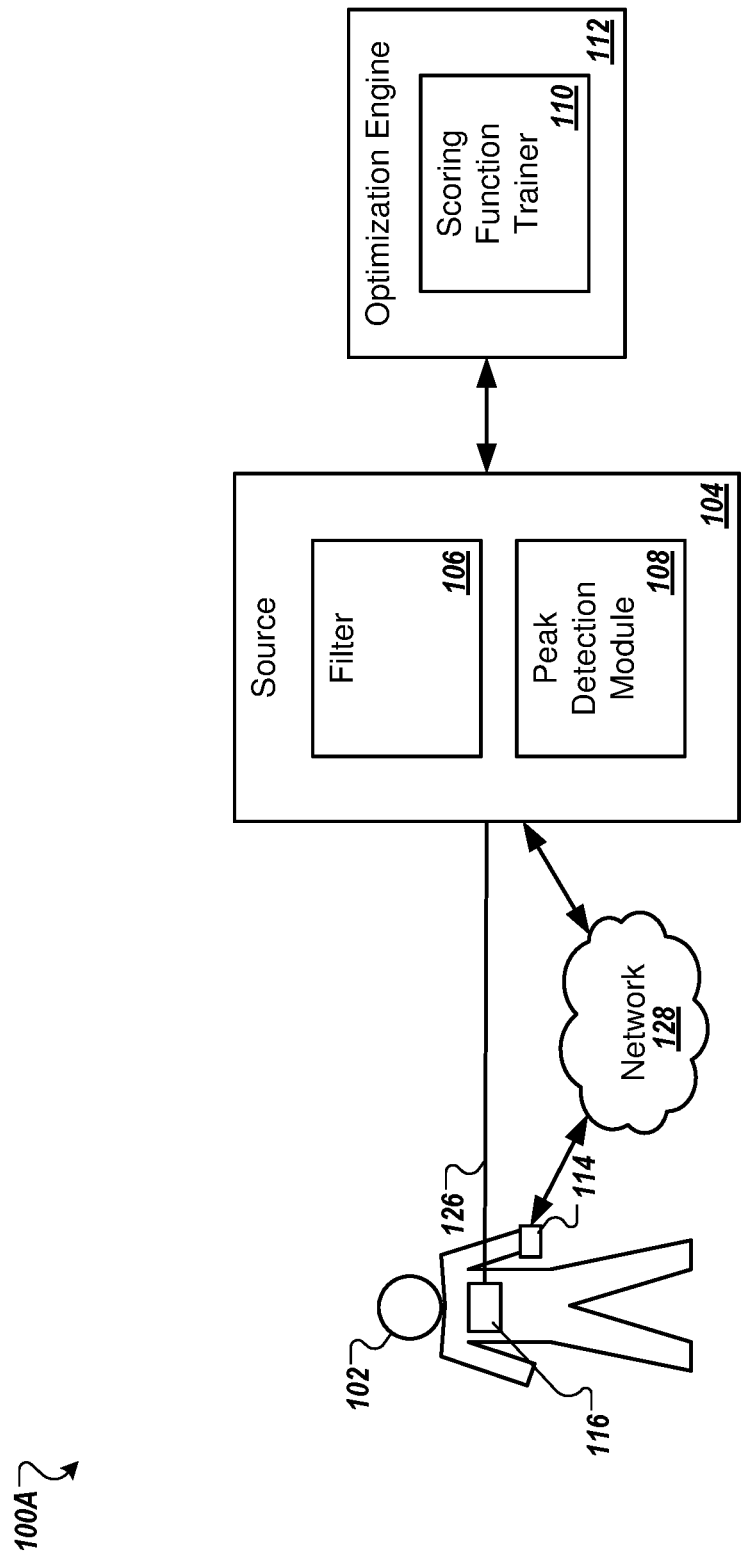
FIG. 1A is a block diagram of a first example environment in which peaks detection in biological data signals may be implemented.

Determination of biologic interval data sets such as heartbeat intervals may be based on detection of real peaks in digital signals derived from a cyclic biological process. The cyclic biological process may include a heartbeat, a chest expansion, or another cyclic biological process. The biologic interval data set being representative of health markers related to a condition of the patient. Conditions of patients may be assessed based on or using the biologic interval data set. Accordingly, it is important to accurately detect real peaks. In many applications, it may be difficult to accurately detect peaks in the digital signal. For example, the digital signals may include many different signal forms that may depend on a sensor type that is measuring the cyclic biological process and/or a sensor location on a body of a user. Additionally, the digital signals may include high frequency noise and/or low frequency noise. The high frequency noise may cause false peaks. The low frequency noise may make it difficult to detect peaks using signal amplitude. Some existing systems use filtering to reduce the noise and to detect peaks. The filtering may reduce the noise, however the filtering may also obscure or remove relevant aspects of the digital signal. Accordingly, it may be difficult to determine other physiological conditions related to the removed or obscured relevant aspects.

Accordingly, embodiments described in the present disclosure relate to peak detection in digital signals that are derived from a cyclic biological process and/or measurement thereof. These embodiments provide an improvement to computing systems that are configured to measure and/or display biological interval data. In particular, the embodiments described in the present disclosure enable accurate detection of the peaks in digital signals that are based on a single scoring function. The scoring function is based on several parameters of the digital signals and optimized through machine learning techniques to suit a particular arrangement of the measurement equipment and physical characteristics of the user.

In detail, some embodiments described in the present disclosure are configured to optimize a scoring function using the machine learning technique. The optimized scoring function may then be applied to digital signals to detect peaks in the digital signals. The scoring function enables a single value to be assigned to peaks within a time range of the digital signal. The peaks may then be compared relative to one another, which may enable selection of a real peak that has a highest score as calculated according to the scoring function.

Additionally, some embodiments described in the present disclosure filter the digital signals prior to application of the scoring function. The filtering is configured to remove or mitigate high frequency and/or low frequency noise. However, the filtering does not obscure features of the digital signals. Instead, features are extracted following the filtering of the digital signal. Moreover, the scoring function incorporates and is based on the extracted features. Accordingly, the embodiments provide a peak detection operation and system that addresses the shortcomings in some existing systems. In particular, the filtering implemented by embodiments of the present disclosure do not obscure or remove features of the digital signal. Additionally, the implementation of the scoring function enables the digital signals to be processed using features that remain in the digital signals following the filtering. Thus, the scoring function reflects the features of the digital signals and detects peaks based at least partially on the features extracted from the digital signals.

Furthermore, embodiments of the present disclosure represent a technologic improvement to current technologies. In particular, current technologies inaccurately detect peaks in digital signals derived from a cyclic biological process (e.g., due to noise in the signal) or the current technologies apply a filter that obscures or removes features of the digital signals. Thus, the embodiments described in the present disclosure provide a technological solution to these and other technological problems in peak detection in digital signals representative of cyclic biological processes.

These and other embodiments are described with reference to the appended figures. In the figures, features and components with the same item number indicate similar function and structure unless described otherwise. The figures are not necessarily drawn to scale.

FIG. 1A is a first example environment 100A in which peak detection of digital signals may be implemented. In the first environment 100A, the digital signals may be derived from a cyclic biological process. The cyclic biological process may include a heartbeat, a chest expansion, or another cyclic biological process of a patient 102. The peak detection implemented in the first environment 100A may be computed in real time or substantially real time. Additionally, the peak detection may involve low computing resources relative to other peak detection processes. Moreover, the peak detection may be suitable for multiple sources (e.g., source 104), multiple types of digital signals, multiple locations of sensors (e.g., 116 and 114), or combinations thereof.

In the first environment 100A, the patient 102 may be fitted with one or more sensors 114 and 116. The sensors 114 and 116 may include an electrical potential sensor, a respiratory sensor, an ultrasound sensor, a PPG sensor, a camera, a mechanical expansion sensor, an acoustic sensor, or another suitable sensor that may receive data representative of the cyclic biological process.

For instance, in some embodiments, a chest sensor 116 may include one or more electrical potential sensors. The chest sensor 116 may measure cardiac electrical potential and communicate a digital signal representative of the cardiac electrical potential to a source 104. The source 104 may detect peaks in the digital signal as described below. Additionally, a mobile sensor 114 may include a finger heart rate monitor, a watch with a heart rate monitor, or another heart rate monitor. The mobile sensor 114 may measure the cyclic biological process and communicate data representative of the cyclic biological process to the source 104.

In the depicted embodiment, the sensors 114 and 116 may be electrically coupled to the source 104 via an electrical and/or an optical cable 126 and/or may be communicatively coupled to the source 104 via a communication network (network) 128. For instance, in FIG. 1, the mobile sensor 114 may be communicatively coupled to the source 104 via the network 128 and the chest sensor 116 may be electrically coupled to the source 104 via the cable 126.

The network 128 may include any network configured for communication of signals between any of the sensors 114 and 116 and the source 104 of the first environment 100A. For instance, the network 128 may include a local area network (LAN), a wide area network (WAN) (e.g., the Internet), and/or other interconnected data paths across which multiple devices may communicate. In some embodiments, the network 128 may include a peer-to-peer network. The network 128 may also be coupled to or include portions of a telecommunications network that may enable communication of data in a variety of different communication protocols. In some embodiments, the network 128 includes or is configured to include a BLUETOOTH® communication network, a Wi-Fi communication network, a ZigBee communication network, an extensible messaging and presence protocol (XMPP) communication network, a cellular communications network, any similar communication networks, or any combination thereof for sending and receiving data. The data communicated in the network 128 may include data communicated via short messaging service (SMS), multimedia messaging service (MMS), hypertext transfer protocol (HTTP), direct data connection, wireless application protocol (WAP), e-mail, or any other protocol that may be implemented with the source 104 and the sensors 114 and 116.

The patient 102 may include any individual, a user, or biological entity such as an animal. In the present disclosure, the patient 102 is depicted as a human, however, it may be appreciated with the benefit of this disclosure that cyclic biological processes occur throughout nature. The patient 102 is not necessarily be under care of a healthcare provider. For instance, in some embodiments, the patient 102 may implement one or more processes described in the present disclosure and perform a self-assessment of a biological condition. The Accordingly, the embodiments described herein may be applicable to animals as well as other biological organisms or systems.

The source 104 may be configured to detect peaks in the digital signals received from the sensors 114 and 116. The source 104 may include a filter 106 and a peak detection module 108. The peak detection module 108 may be configured to use a scoring function to detect peaks in the digital signal. The scoring function may combine and weigh multiple features or combinations of features of the digital signals into a single value.

For example, the scoring function may include a linear combination of constants and features or a linear combination of constants and parameters that are based on the features. The features may be based on characteristics or may be representative of characteristics of the digital signals. For instance, in some embodiments, the scoring function may be represented by a general scoring expression:

$$Score = c_1 F_1 + c_2 F_2 + \ldots c_n F_n$$

In the general scoring expression, $F_1, F_2, F_n$ are parameters, which may be based on the features. Some examples of the parameters are provided below. For example, $F_1, F_2, F_n$ may include $F_{hm}, F_{hl}, F_{hr}, F_{tm}, F_{sl},$ and $F_{sr}$, which are described below. The parameter Score represents a peak score. The parameters $c_1, c_2,$ and $c_n$ represent constants.

The constants may be selected arbitrarily, may be selected without knowledge of peaks in the digital signals, may be selected using trial and error, may each be set to 1, may be optimized, or some combination thereof. For instance, in some embodiments, the scoring function used by the peak detection module 108 may be optimized. Some additional details of the optimization of the scoring function are provided elsewhere in the present application.

In the embodiment of FIG. 1A, the scoring function may be optimized by an optimization engine 112. The optimization engine 112 may include a scoring function trainer 110. The scoring function trainer 110 may iteratively communicate training signals to the source 104. The training signals may include peaks that may be known and marked as well as one or more features that describe properties of the peaks. The peak detection module 108 may detect peaks in the training signals. Detected peaks and extracted features may be compared with the marked peaks and/or marked features of the training signals. Based on this comparison, the scoring function of the peak detection module 108 may be optimized. For instance, one or more of the constants in the scoring function may be updated and optimized by a machine learning technique. The machine learning technique may include a linear regression technique, a support vector machine, logistic regression, Naïve Bayes, or another suitable technique for fitting linear systems.

The optimization engine 112 may be implemented for each arrangement of measurement equipment and/or type of equipment. For instance, the source 104 may include an ECG that measures heart beats based on a 12 lead chest sensor set. The optimization engine 112 may optimize the scoring equation for this arrangement. Additionally, the source 104 may include a photoplethysmogram (PPG) that receives measurements from an earlobe. The optimization engine 112 may optimize the scoring function for this arrangement as well. In yet other embodiments, the source 104 may include a mobile device (some details of which are provided below). In these and other examples, the same scoring function may be used, but the constants in the scoring function may be different.

After the optimization engine 112 optimizes the scoring function, the source 104 may be configured to use the optimized scoring function to detect peaks in a digital signal received from the sensors 114 and 116. For instance, in some embodiments, the filter 106 may be configured to filter noise from the digital signals. The filter 106 may include a bandpass filter, which may be configured to filter at least a portion of high frequency noise and/or a portion of low frequency noise. The filter 106 may communicate a filtered digital signal to the peak detection module 108.

The peak detection module 108 may be configured to select a time range of an input signal that includes the digital signal. The time range may be based on underlying physiological properties of the source 104, the patient 102, the sensors 114 and 116, or some combination thereof. In some embodiments, the time range may be in a range of about 0.3 seconds (s) to about 1.5 s. The peak detection module 108 may be configured to identify candidate peaks and troughs within the selected time range. The peak detection module 108 may extract one or more features of the digital signal. The features may describe properties of the two or more candidate peaks.

The candidate peaks may be scored using the scoring function. The scoring function may include a linear combination of a set of parameters that are based on the features extracted from the digital signal. In some embodiments, each of the set of parameters include a value between zero and one. In these and other embodiments, having the values of the set of parameters being between zero and one may enable linear combinations of the parameters. A value of zero may indicate that a parameter is calculated for a point that is unlikely to be a peak. A value of one may indicate that a parameter is calculated for a point that is likely to be a peak. The peak with the highest score as calculated according to the scoring function may be selected as a real peak.

The peak detection module 108 may then generate a biologic interval data set that includes the real peak and at least one other peak. The biologic interval data set may be representative of health markers related to a condition of the patient. An example of the biologic interval data set may include a heart rate or a heart rate variability data set. Other biologic interval data sets may include respiratory intervals, chest expansion intervals, and the like. The conditions of the patient may be assessed based on the biologic interval data set.

The peak detection module 108, the optimization engine 112, and one or more components or modules thereof described throughout the present disclosure may be implemented using hardware including a processor, a microprocessor (e.g., to perform or control performance of one or more operations), a field-programmable gate array (FPGA), or an application-specific integrated circuit (ASIC). In some other instances, peak detection module 108, the optimization engine 112, and one or more components or modules thereof may be implemented using a combination of hardware and software. Implementation in software may include rapid activation and deactivation of one or more transistors or transistor elements such as may be included in hardware of a computing system (e.g., depicted in FIG. 6). Additionally, software defined instructions may operate on information within transistor elements. Implementation of software instructions may at least temporarily reconfigure electronic pathways and transform computing hardware.

Modifications, additions, or omissions may be made to the first environment 100A without departing from the scope of the present disclosure. For example, the first environment 100A may include one or more sources 104, one or more optimization engines 112, one or more sensors 114 and 116, or any combination thereof. Moreover, the separation of various components and servers in the embodiments described herein is not meant to indicate that the separation occurs in all embodiments. For example, in some embodiments, the optimization engine 112 may be included in the source 104. Moreover, it may be understood with the benefit of this disclosure that the described components and servers may generally be integrated together in a single component or server or separated into multiple components or servers. For example, the filter 106 and the peak detection module 108 may be implemented in another computing device that is communicatively coupled to the source 104 and/or the sensors 114 and 116.

Figure 1B:
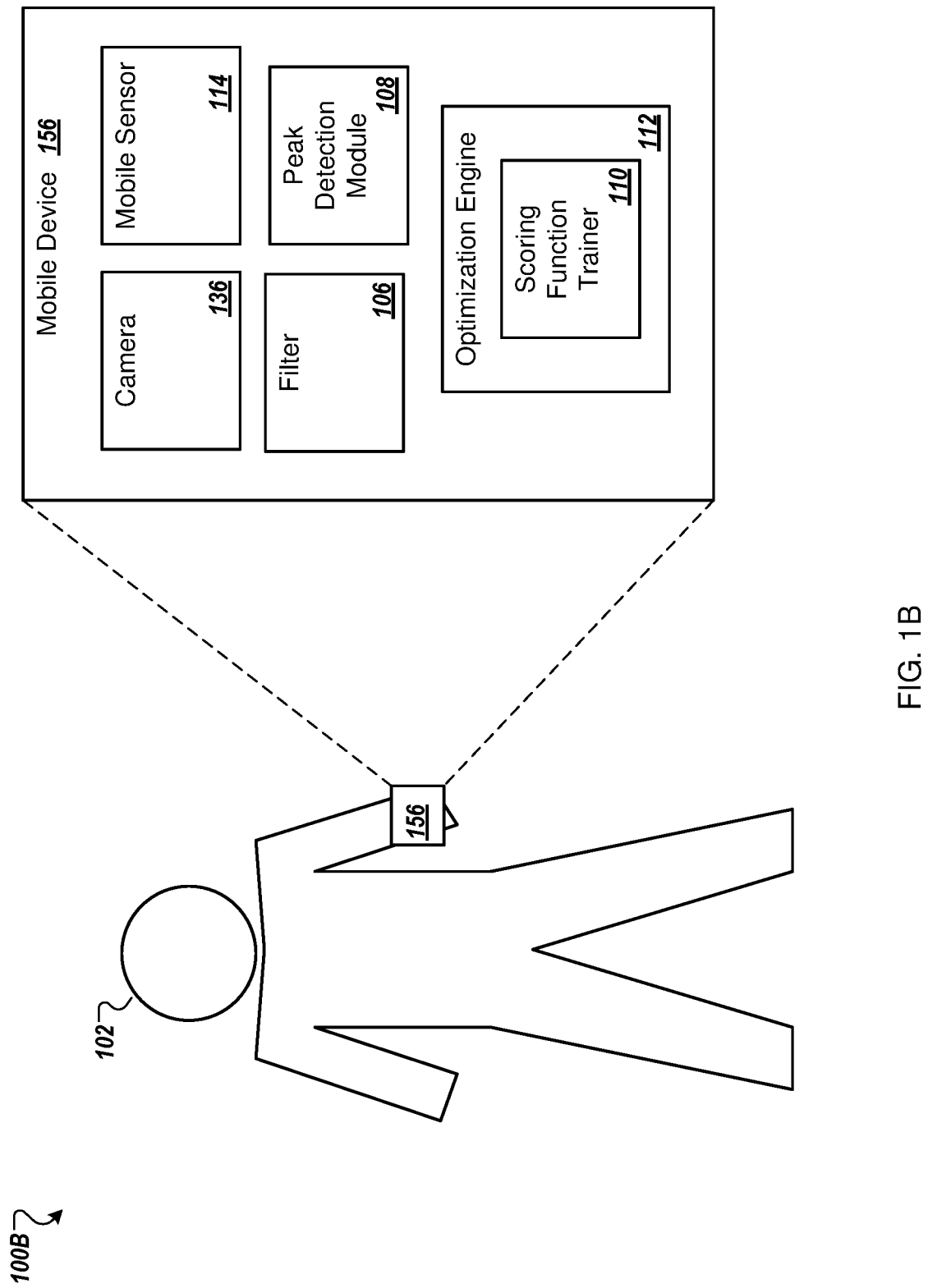
FIG. 1B is a block diagram of a second example environment in which peaks detection in biological data signals may be implemented.

FIG. 1B illustrates a second example environment 100B in which peak detection of digital signals may be implemented. In the second environment 100B, the digital signals may be derived from a cyclic biological process of the patient 102. The second environment 100B may include the patient 102 and a mobile device 156.

The mobile device 156 may be configured to obtain the digital signals and to detect peaks in the digital signals. For instance, the mobile device 156 may include the filter 106, the peak detection module 108, the optimization engine 112, the scoring function trainer 110, or some combination thereof. The filter 106, the peak detection module 108, the optimization engine 112, and the scoring function trainer 110 may function substantially as described with reference to FIG. 1A.

To obtain the digital signals, the mobile device 156 may include a camera 136 and/or the mobile sensor 114. The mobile device 156 may be configured to obtain data representative of the cyclic biological process using the camera 136 and/or the mobile sensor 114. The camera 136 and/or the mobile sensor 114 may communicate the digital signal to the filter 106 and/or the peak detection module 108. The peak detection module 108 may output peaks, which may be used to determine and display a heart rate or a heart rate variability.

For instance, in some embodiments, the camera 136 may be implemented as a PPG sensor. An example of the PPG sensor may include a pulse oximeter. The camera 136 may measure data represented in a PPG. The data in the PPG may then be communicated to the filter 106 and/or the peak detection module 108. The peak detection module 108 may detect peaks in the received data as described elsewhere in the present disclosure. Additionally, in some embodiments, the mobile sensor 114 may be configured to measure data representative of the digital signal. For instance, the mobile sensor 114 may be configured to measure or monitor a heart interval when in contact with the patient 102. The mobile sensor 114 may communicate data representative of the heart interval to the peak detection module 108.

In the embodiment of FIG. 1B, the mobile sensor 114 is included in the mobile device 156. In some other embodiments, the mobile sensor 114 may be separate from and in communication with the mobile device 156. For instance, the mobile sensor 114 may be a communicate with the mobile device 156 via a network (e.g., the network 128). For example, in some embodiments, the mobile sensor 114 may include an external wireless sensor that is connected to the mobile device 156 using a BLUETOOTH® communication protocol.

In some embodiments, the mobile device 156 may include a smart phone, tablet portable computer, or another mobile device. In these and other embodiments, the mobile device 156 may be placed in contact with the patient 102 or placed relative to the patient 102 to enable measurement of the cyclic biological process. Additionally, in some embodiments, the mobile device 156 may include a smart watch, a wearable device, a heart rate chest monitor, a fitness tracker, or another mobile device. In these and other embodiments, the mobile device 156 may be worn by the patient 102.

Modifications, additions, or omissions may be made to the second environment 100B without departing from the scope of the present disclosure. For example, the second environment 100B may include one or more sources 104, one or more optimization engines 112, one or more mobile sensors 114, or any combination thereof. Moreover, the separation of various components and servers in the embodiments described herein is not meant to indicate that the separation occurs in all embodiments. Moreover, it may be understood with the benefit of this disclosure that the described components and servers may generally be integrated together in a single component or server or separated into multiple components or servers. For example, the optimization engine 112 may be located remotely to the mobile device 156 and communicate with the mobile device via a network such as the network 128.

Figure 2:
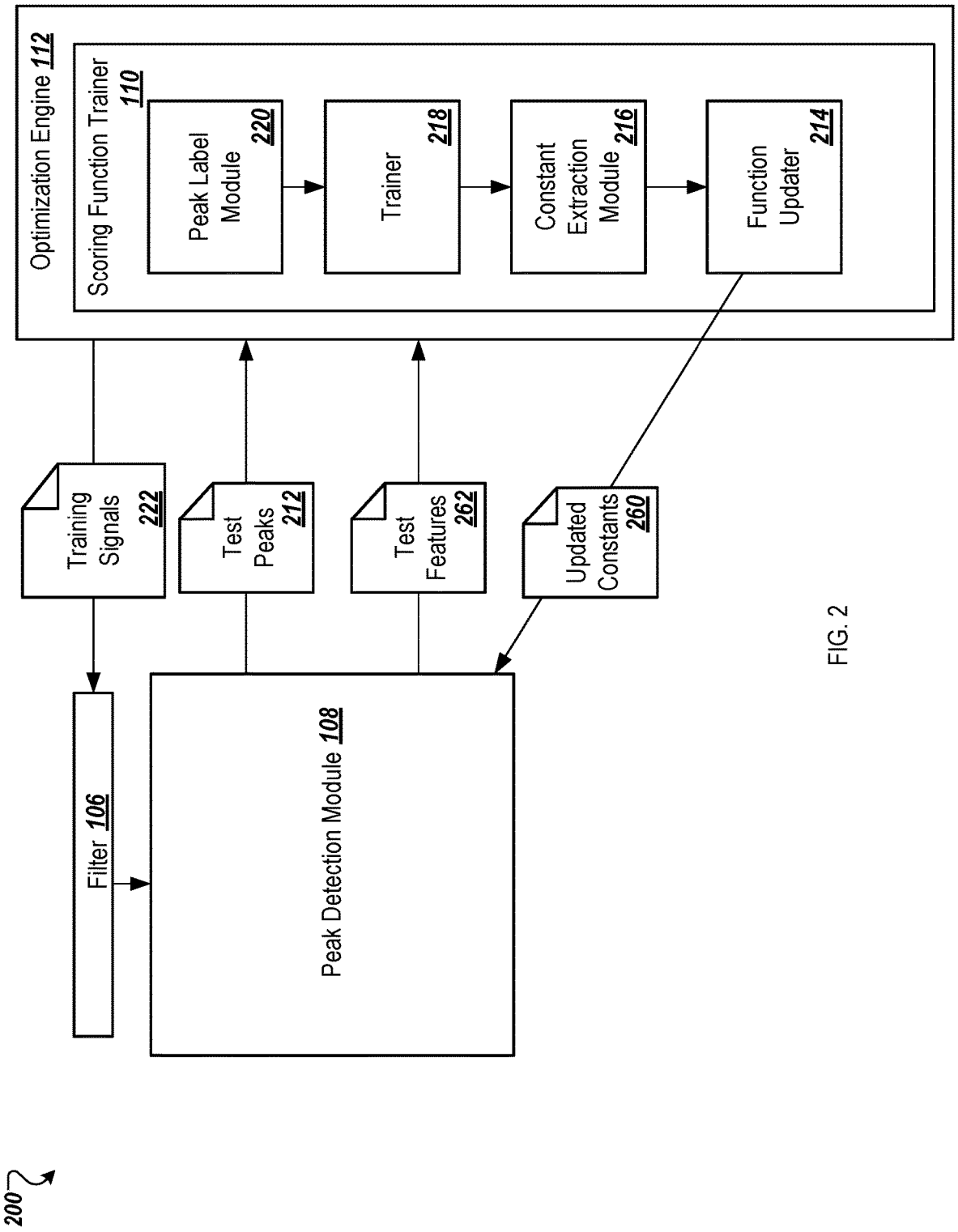
FIG. 2 depicts an example scoring function optimization process that may be implemented in the environments of FIGS. 1A and 1B.

FIG. 2 depicts an example scoring function optimization process (optimization process) 200 that may be implemented in the first environment 100A or the second environment 100B of FIGS. 1A and 1B. The optimization process 200 may involve the filter 106, the peak detection module 108, and the optimization engine 112 described with reference to FIGS. 1A and 1B.

The communication in the optimization process 200 may be implemented via a communication network such as the network 128 of FIGS. 1A and 1B. Additionally or alternatively, communication in the optimization process 200 may be via a cable such as the cable 126 of FIGS. 1A and 1B. Additionally, in some embodiments the filter 106, the peak detection module 108, and the optimization engine 112 may be included in a single computing device (e.g., the mobile device 156 or the source 104). For instance, the source 104 of FIG. 1A may include an echocardiogram (ECG). The ECG may include the filter 106, the optimization engine 112, and the peak detection module 108.

Generally, the optimization engine 112 may be configured to implement a machine learning technique to optimize one or more portions of a scoring function. The machine learning technique based on training signals 222.

The training signals 222 may be representative of a cyclic biological process. In some embodiments, the training signals 222 may be simulated data. In other embodiments, training signals 222 may be data representative of an actual measured cyclic biological process. The training signals 222 may include peaks that are known and/or labelled. The training signals 222 may include known features.

The training signals 222 may be communicated to the filter 106. The filter 106 may be configured to filter the training signals 222 to remove low frequency noise and high frequency noise. Filtering of the low frequency noise may reduce changes in amplitude of the training signals 222 over time and/or change in a mid-point of the training signals 222 over time. Filtering of high frequency noise may remove "choppiness" in the training signals 222.

The peak detection module 108 may be configured to select a time range of the training signals 222. The peak detection module 108 may identify candidate peaks and troughs within the selected time range of the training signal 222 and extract a feature that describes properties of the candidate peaks. The peak detection module 108 may score the candidate peaks using the scoring function and output detected test peaks 212 from the training signals 222 to the optimization engine 112. The peak detection module 108 may further output test features 262 that may include features found for the training signals 222.

The test peaks 212 and the test features 262 output by the peak detection module 108 may be received by the scoring function trainer 110 of the optimization engine 112. The scoring function trainer 110 may include a peak label module 220, a trainer 218, a constant extraction module 216, a function updater 214, or some combination thereof. The peak label module 220 may be configured to find and label candidate peaks to indicate whether the test peaks 212 correspond to the known/labelled peaks in the training signals 222.

The trainer 218 may be configured to train a classifier based on labelled features. For instance, the trainer 218 may compare the test features 262 to known features in the training signals 222. The constant extraction module 216 may be configured to extract constants from the trained classifier of the trainer 218. The function updater 214 may be configured to update the scoring function with updated constants 260 that are extracted from the trained classifier.

For instance, the scoring function may be represented by a linear scoring function expression:

$$Score_{p\_i}=c_1F_{hm}+c_2F_{hl}+c_3F_{hr}+c_4F_{tm}+c_5F_{sl}+c_6F_{sr};$$ in which:

in the linear scoring function expression, $c_1$-$c_6$ are constants. The parameters $F_{hm}$, $F_{hl}$, $F_{tm}$, $F_{sl}$, and $F_{sr}$ are parameters based on the features, which are described elsewhere in the present disclosure. The parameter $Score_{p\_i}$ represents a candidate peak score.

Figure 3:
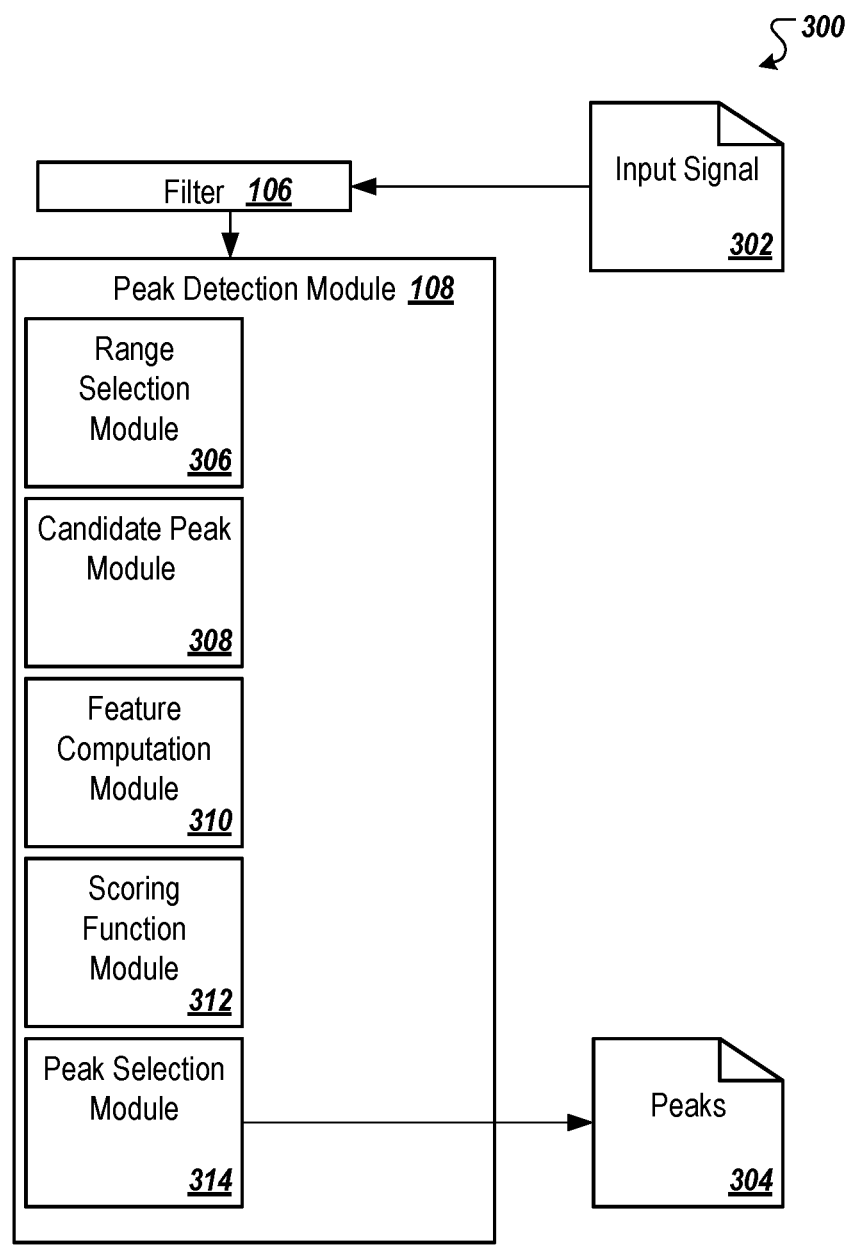
FIG. 3 depicts an example peak detection process that may be implemented in the environments of FIGS. 1A and 1B.

FIG. 3 illustrates a peak detection process 300 that may be implemented in environments 100A and 100B of FIGS. 1A and 1B. The peak detection process (detection process) 300 may be performed following optimization of a scoring function or following the selection of values for constants used in the scoring function. An example of an optimization process is described with reference to FIG. 2. Other optimization processes may also be implemented and/or an optimization process may be implemented with a selection process.

The detection process 300 may be performed by the filter 106 and the peak detection module 108 described above. The peak detection module 108 may include a range selection module 306, a candidate peak module 308, a feature computation module 310, a scoring function module 312, a peak selection module 314, or some combination thereof. The range selection module 306, the candidate peak module 308, the feature computation module 310, the scoring function module 312, and the peak selection module 314 may be collectively referred to as detection modules.

Figure 4:
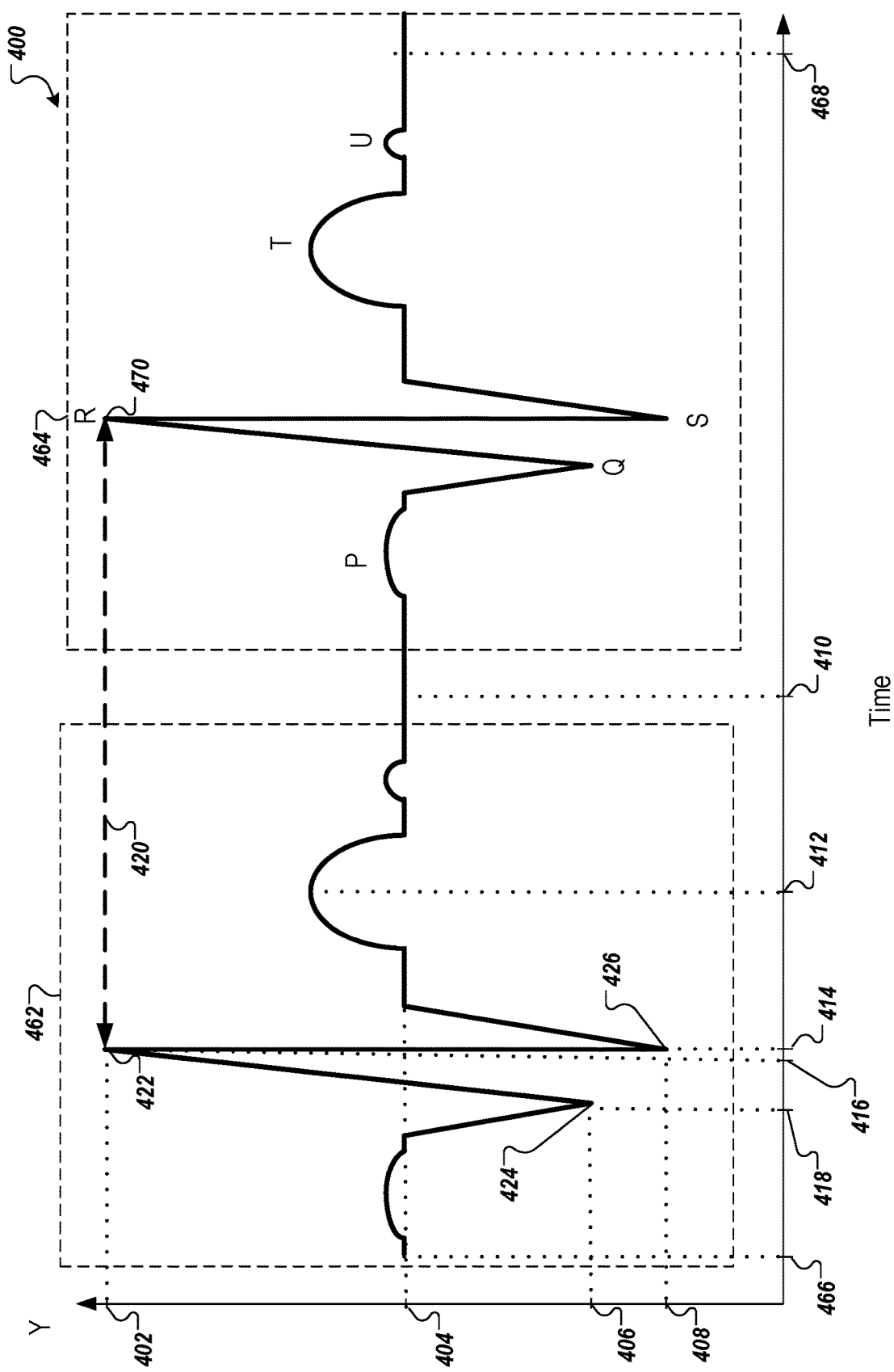
FIG. 4 depicts an example biological data signal that may be processed in the environments of FIGS. 1A and 1B.
Figure 5A:
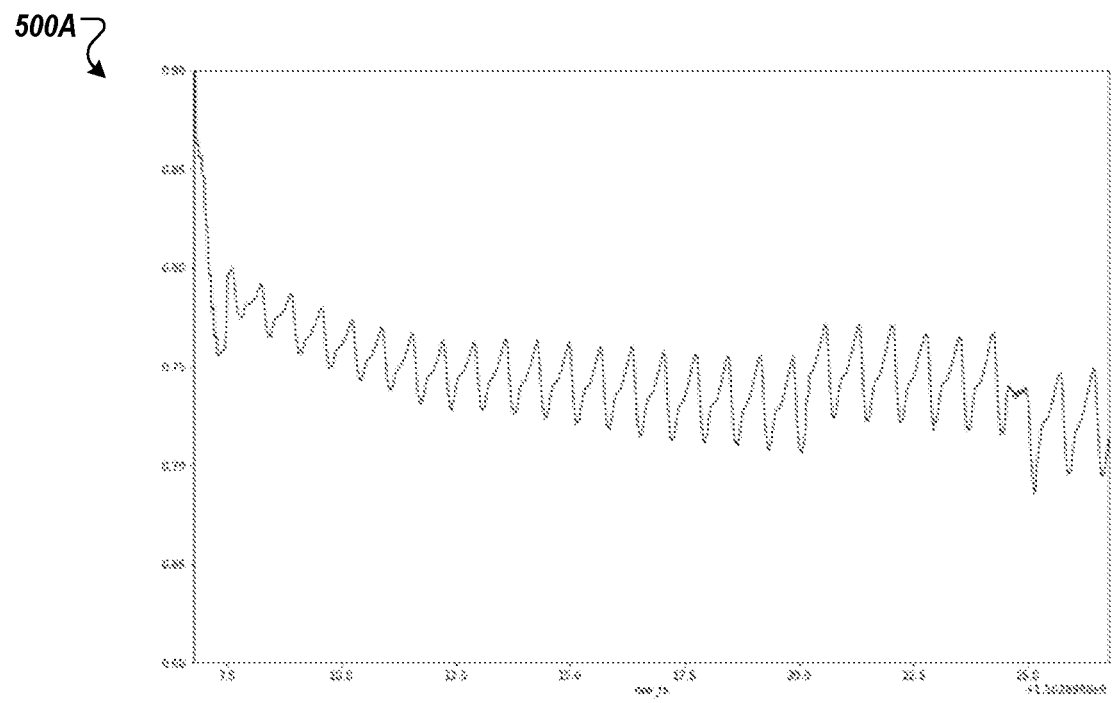
FIGS. 5A-5D depict other example biological data signals that may be processed in environments of FIGS. 1A and 1B.
Figure 5B:
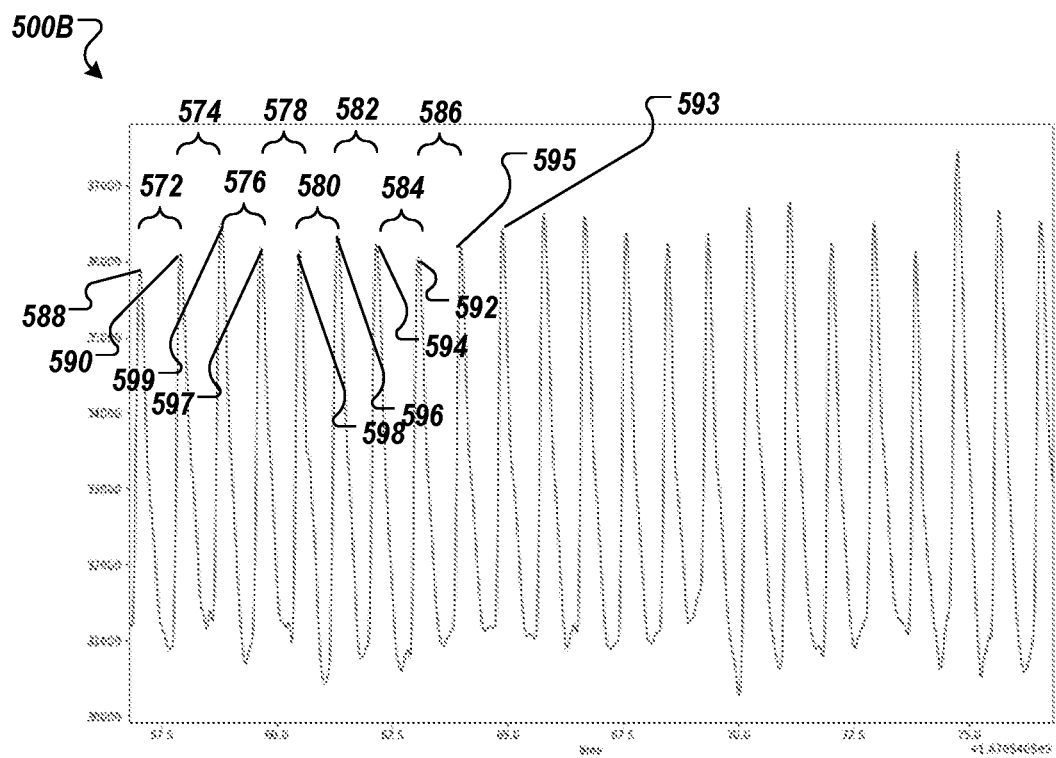
Figure 5C:
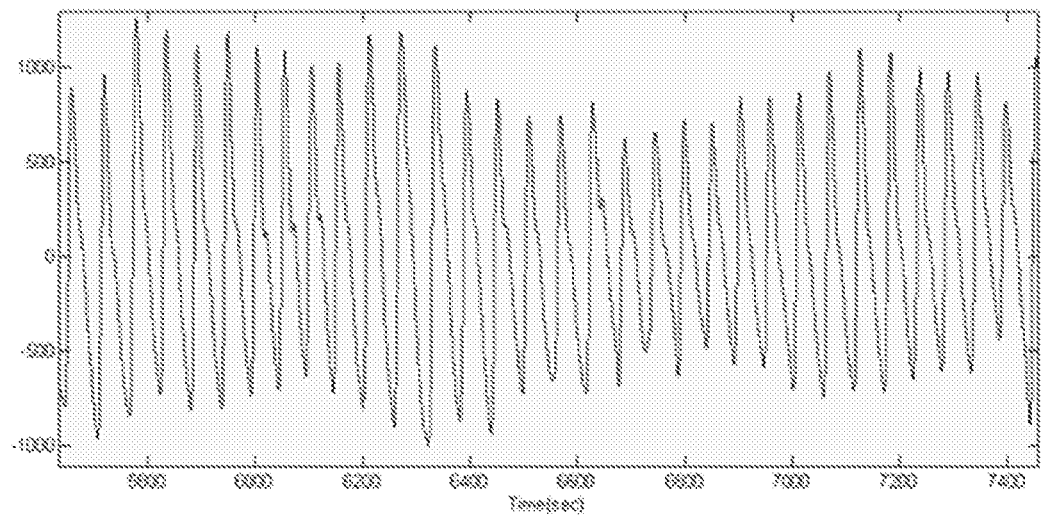
Figure 5D:
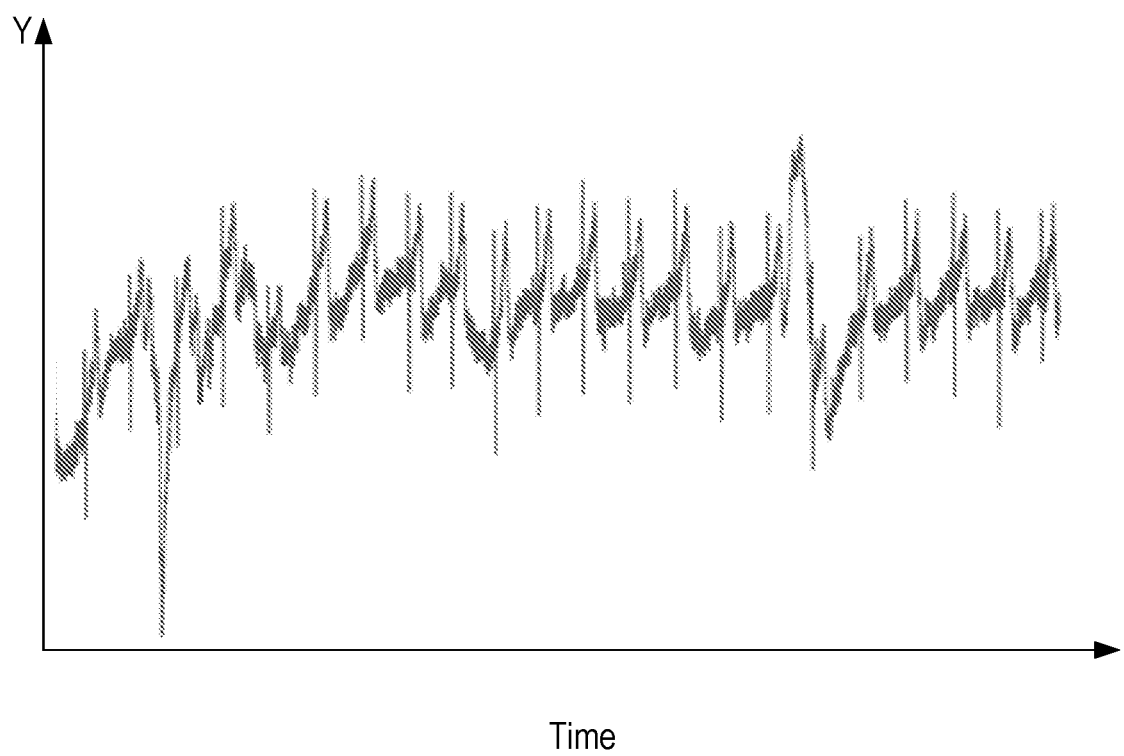

In the detection process 300, the filter 106 may be configured to receive an input signal 302. The input signal 302 may include a digital signal derived from a cyclic biological process that is measured from a sensor. Some examples of the input signal 302 are depicted in FIGS. 4-5D. For instance, FIG. 4 depicts an example biological data signal 400 that may be an ECG waveform. FIG. 5A depicts a first data signal 500A that is representative of a PPG measured from a fingertip. FIG. 5B depicts a second data signal 500B that is representative of a PPG measured from a finger cuff. FIG. 5C depicts a third data signal 500C that is representative of a PPG measured from an earlobe of a user. FIG. 5D depicts a fourth data signal 500D that is representative of an ECG measured from a fingertip of a user.

The filter 106 may be configured to filter the input signal 302 to remove low frequency noise and high frequency noise. As described elsewhere in the present disclosure, filtering of the low frequency noise may reduce changes in amplitude of the input signal 302 over time and/or change in a mid-point of the input signal 302 over time. For example, the first data signal 500A of FIG. 5A includes low frequency noise that may change the amplitude of the first data signal 500A, which may be filtered by the filter 106.

Filtering of high frequency noise may remove "choppiness" in the input signal 302. For example, the fourth data signal 500D of FIG. 5D includes high frequency noise that may be filtered by the filter 106. For example, in some implementations, such as an ECG or PPG, the input signal 302 may include a frequency in a range of about 0.7 Hertz (Hz) and about 4 Hz. In these and other implementations, portions of the input signal 302 outside the range may be removed.

In some embodiments, the filter 106 may be configured to convert the input signal 302. For example, responsive to the input signal 302 that includes a digital signal not being sampled at regular intervals, the filter 106 may be configured to convert the digitized signal to regular interval samples using linear interpolation. In these and other embodiments, the filter 106 may then generate a set of median values based on interpolated data. For instance, for each of the interpolated data points, the filter 106 may find a first median. The first median may be found for a first number of preceding interpolated data points including a current interpolated data point. For example, if the first median is found for a $400^{th}$ interpolated data point, the first median may include a median value found for a set of interpolated data points that include the $301^{st}$ to the $400^{th}$ interpolated data point. The filter 106 may then find a current second value. The second value may be equal to a difference between the current interpolated data point and the first median. The filter 106 may then find a second median. The second median may be equal to a second number of preceding second values including the current second median. For example, the second value may be the $25^{th}$ second value. The second median may be found for a set of second values from the $21^{st}$ second value to the $25^{th}$ second value. The filter 106 may then output the second median.

The range selection module 306 may be configured to select a time range of the input signal 302. The time range may be based on underlying physiological properties of a source or user from which the input signal 302 is obtained.

For instance, in embodiments in which the source (e.g., 104 of FIG. 1A) includes an ECG or a PPG, the underlying physiological property may include a rate at which a heart muscle contracts and expands. In general, a human heart rate may be in the range from about thirty beats per minute to about two-hundred beats per minute. The far end (two-hundred beats per minute) of the range may represent abnormal conditions such as an in-progress heart attack (myocardial infarction) or a highly trained athlete. At two-hundred beats per minute, an inter-beat interval may be about three-hundred milliseconds (ms). At thirty beats per minute, an inter-beat interval may be about 2000 ms. Accordingly, based on these characteristics, peak intervals may be selected based on the inter-beat intervals. For instance, if a first peak occurs at a time T1, then the next peak may be in the range of about T1+300 ms to about T1+2000 ms. Other physiological properties may have other ranges. For example, a mobile sensor may be configured to measures the rise and fall of a chest of a user to determine breathing rate. Breathing rate is determined by the lungs and the muscles in the chest. This physiological property may have a different range than the ECG and PPG signals.

The candidate peak module 308 may be configured to identify candidate peaks and troughs within the selected time range. For example, the candidate peak module 308 may find peaks and troughs within the selected time range. In these and other embodiments, the peaks may each include a sequence of one or more samples of the same value in which the sample immediately preceding the sequence has a lower value and the sample immediately following the sequence also has a lower value. The troughs may each include a sequence of one or more samples of the same value in which the sample immediately preceding the sequence has a higher value and the sample immediately following the sequence also has a higher value. The candidate peak module 308 may store the peaks and the troughs as a list of peaks and troughs. In the list of peaks and troughs, each point may include a timestamp, a sample value, and an indication of whether the point is a peak or a trough.

After the candidate peaks are identified and stored in the list of peaks and troughs, the candidate peak module 308 may be configured to combine one or more nearby peaks. As used herein, "nearby peaks" may include immediately adjacent peaks or peaks within a few (e.g., two or three) peaks. In some embodiments, to combine the nearby peaks, the candidate peak module 308 may compute a difference ($y_{diff}$) between a highest sample value and a lowest sample value over the time range. An example of the highest sample value and the lowest sample value are provided with reference to FIG. 4. The candidate peak module 308 may then search through adjacent peaks in the list of peaks and troughs. The candidate peak module 308 may combine adjacent peaks $p_i$ and $p_j$. For example, The candidate peak module 308 may determine a time difference between centers of the adjacent peaks $p_i$ and $p_j$. Additionally, the candidate peak module 308 may be configured to determine whether the following inequalities are met:

$$(y_i - y_{ti})/y_{diff} < 0.1 \text{ or } (y_j - y_{ti})/y_{diff} < 0.1$$

In the inequalities, $y_i$ represents the sample value of peak $p_i$, $y_j$ represents the sample value of peak $p_j$, and $y_{ti}$ is the sample value of the trough $t_i$ between peaks $p_i$ and $p_j$. In response to the time difference between centers of the two peaks being less than a minimum time threshold, $T_{min}$, and $(y_i - y_{ti})/y_{diff} < 0.1$ or $(y_j - y_{ti})/y_{diff} < 0.1$, the adjacent peaks may be selected for combination.

In some embodiments, the candidate peak module 308 may determine replacement inequalities:

$$y_i > y_j \text{ and } y_{ti} < y_{tj}; \text{ and}$$

$$y_i > y_j \text{ and } y_{ti} >= y_{tj}.$$

In the replacement inequalities, the parameters are as described above. Based on the replacement inequalities the candidate peak module 308 may perform combinations according to the following combination expressions:

--- if ($y_i > y_j$ and $y_{ti} < y_{tj}$)
  then {replace
    $p_i$, $t_i$, $p_j$, and $t_j$ in the list of peaks and troughs with $p_i$ and $t_i$}
else if ($y_i > y_j$ and $y_{ti} >= y_{tj}$)
  then {replace
    $p_i$, $t_i$, $p_j$, and $t_j$ in the list of peaks and troughs with $p_i$ and $t_j$}
else {replace
    $p_i$, $t_i$, $p_j$, and $t_j$ in the list of peaks and troughs with $p_j$ and $t_j$}.

---

The candidate peak module 308 may continue to perform the combination expressions until there initial inequalities are no longer satisfied.

The feature computation module 310 may be configured to extract a feature that describes properties of the two or more candidate peaks following the combinations of the peaks. For example, with reference to FIG. 4 several features are depicted. FIG. 4 depicts an example biological data signal (signal) 400 that may be processed in the environments 100A and 100B of FIGS. 1A and 1B. The signal 400 may be representative of two cycles 462 and 464 of a cyclic biological process. A first cycle 462 may be separated by a second cycle 464 at about time 410. The second cycle 464 is labelled according to a QRS complex. The first cycle 462 is labelled with multiple features, which may be extracted during a peak detection process.

A first feature may include a length of time over which candidate peaks are considered, $T_{range}$. In FIG. 4, the length of time may include a time period from an initial time 466 to a final time 468 for the first cycle 462 and the second cycle 464. In the example of FIG. 4, two cycles 462 and 464 may be included in the length of time. In other embodiments two or more cycles may be included in the length of time. In some embodiments, the length of time may be in a range of about 0.3 seconds to about 1.5 seconds.

A second feature may include a minimum sample value over the time range. The minimum sample value may be referred to using $y_{min}$. In FIG. 4, the mimimum sample value may be found at a first point 426 of the first cycle 462. The first point 426 may include a lowest point (having the lowest y-value) in the first cycle 462 and the second cycle 464. The second sample value may be equal to the y-value of the first point 426. The y-value of the first point 426 is labelled 408 in FIG. 4.

A third feature may include a maximum sample value over the time range. The maximum sample value may be referred to using, $y_{max}$. In FIG. 4, the maximum sample value may be found at second point 422 of the first cycle 462. The second point 422 may include a highest point in the first cycle 462 and the second cycle 464. The maximum sample value may be equal to a y-value of the second point 422. The y-value of the second point 422 is labelled 402 in FIG. 4.

The fourth feature may include a sample value for a peak. In FIG. 4, the peak may correspond to the second point 422 (referred to hereinafter, as "peak 422") or to a third point 470. The peak 422 may be indexed by an indexing variable (e.g., i or j). The peak 422 may be referred to using, p_i or p_j. The remaining features are described with reference to the peak 422, but may be extracted for one or more other peaks in the digital signal 400. The sample value for the peak 422 may include the y-value of the peak 422. In FIG. 4, the y-value of the peak 422 is labelled 402. The fifth feature may include a timestamp for the peak 422. The timestamp for the peak 422 may be referred to using, $t_{p\_i}$. In FIG. 4, the timestamp for the peak 422 may include the x-value of the peak 422. In FIG. 4, the x-value of the peak 422 is labelled 416.

A sixth feature may include a sample value for a trough preceding the peak 422. In FIG. 4, the trough preceding the peak 422 may be at point 424. The trough 424 preceding the peak 422 may be referred to using t_left. The sample value for the trough 424 may be referred to using $y_{t\_left}$. The sample value for the trough 424 preceding the peak 422 may include the y-value of the trough 424. In FIG. 4, the y-value of the trough 424 is labelled 406. A seventh feature may include a timestamp of the trough 424. The timestamp of the trough 424 may be referred to using, $t_{p\_left}$. The timestamp for the trough 424 preceding the peak 422 may include the x-value of the trough 424. In FIG. 4, the x-value of the trough 424 is labelled 418.

An eighth feature may include a sample value for a trough following the peak 422. In FIG. 4, the trough following the peak 422 may be at point 426. The trough 426 following the peak 422 may be referred to using, t_right. The sample value for the trough 426 may be referred to using $y_{t\_right}$. The sample value for the trough 426 following the peak 422 may include the y-value of the trough 426. In FIG. 4, the y-value of the trough 426 is labelled 406. A ninth feature may include a timestamp of the trough 426. The timestamp of the trough 426 may be referred to using notation, $t_{p\_right}$. The timestamp for the trough 426 following the peak 422 may include the x-value of the trough 426. In FIG. 4, the x-value of the trough 426 is labelled 414.

A tenth feature may include a left slope. The left slope may equal the slope between the trough 424 and the peak 422. The left slope may be determined according to an example left slope expression:

$$Slope_{i\_left} = (y_{p\_i} - y_{t\_left})/(t_{p\_i} - t_{t\_left}).$$

In the left slope expression, the parameter $Slope_{i\_left}$ represents the left slope. The remaining parameters correspond to the features described above.

An eleventh feature may include a right slope. The right slope may equal the slope between the peak 422 and the trough 426. The right slope may be determined according to an example right slope expression:

$$Slope_{i\_right} = (y_{right} - y_{p\_i})/(t_{right} - t_{p\_i}).$$

In the left slope expression, the parameter $Slope_{i\_right}$ represents the right slope. The remaining parameters correspond to the features described above.

A twelfth feature may include a difference between the highest sample value and the lowest sample value of the time range. For instance in FIG. 4, the difference may be equal to the difference between the maximum sample value (in FIG. 4, 402) and the minimum sample value (in FIG. 4, 408).

A thirteenth feature may include a maximum slope. The maximum slope may be referred to using, $Slope_{max}$. The maximum slope may be calculated according to a maximum slope expression:

for all peaks (p_i)

$$Slope_{max} = Max_i(Max(Slope_{i\_left}, Slope_{i\_right})).$$

In the maximum slope expression $Slope_{max}$ represents the maximum slope. Max represents a maximizing function.

A fourteenth feature may include a timestamp of the expected location of a peak. The timestamp of the expected location may be referred to using $t_{exp}$. The timestamp of the expected location may be computed by finding a median of a particular number (e.g., about 10 or another suitable number) of immediately preceding computed peak intervals and adding the median to a timestamp of an immediately preceding peak. The timestamp of the expected location may be illustrated in FIG. 5B. FIG. 5B depicts a second example data signal 500B that may be representative of a PPG taken from a finger cuff of a user. The second data signal 500B includes intervals 572, 574, 576, 578, 580, 582, 584, and 586 between peaks 588, 590, 599, 597, 598, 596, 594, 592, and 595. To compute the timestamp of the expected location for peak 593, a median of the intervals 572, 574, 576, 578, 580, 582, 584, and 586 may be found. In this example, the particular number is eight. In other examples, the particular number may be less than eight or greater than eight. The median of the intervals 572, 574, 576, 578, 580, 582, 584, and 586 may be added to a timestamp (x-value) of peak 595 that immediately precedes peak 593.

A fifteenth feature may include a minimum sample value. The mimimum sample value may be referred to using $T_{min}$. The minimum sample value may be based on heuristics in some embodiments. For example, referring to FIG. 4, the minimum sample value may be no greater than a minimum signal interval of the data signal 400. Additionally, if the minimum sample value is too small, then high frequency noise may obscure actual peaks in the data signal 400. Moreover, if the minimum sample value is too large, peaks from different cycles may be combined. For instance, in embodiments including the minimum sample value for an ECG or a PPG may be between about 200 and about 300 milliseconds.

Referring back to FIG. 3, the scoring function module 312 may be configured to score the remaining candidate peaks following the combination of the peaks using a scoring function. The scoring function may be a linear function that includes a set of parameters that are weighted according to constants. In some embodiments, the constants are selected arbitrarily, selected without knowledge of peaks in the digital signals, selected using trial and error, or set to 1. Additionally or alternatively, the constants may be optimized.

For example, in some embodiments, the set of parameters may include a height above minimum parameter, a left height parameter, a right height parameter, a closeness to median parameter, a scaled left slope parameter, and a scaled right slope parameter. Referring to FIGS. 3 and 4, the height above minimum parameter may be represented by a height above minimum parameter expression:

$$F_{hm} = (y_{p\_1} - y_{min})/(y_{max} - y_{min}).$$

In the height above minimum parameter expression, $F_{hm}$ represents height above minimum parameter. The remaining parameters are described above. The left height parameter may be represented by a left height parameter expression:

$$F_{hl} = (y_{p\_i} - y_{t\_left})/(y_{max} - y_{min}).$$

In the left height parameter expression, $F_{hl}$ represents the left height parameter. The remaining parameters are described above. The right height parameter may be represented by a right height parameter expression:

$$F_{hr} = (y_{p\_i} - y_{t\_right})/(y_{max} - y_{min}).$$

In the right height parameter expression, $F_{hr}$ represents the right height parameter. The remaining parameters are described above. The closeness to median parameter may be represented by a median parameter expression:

$$F_{tm} = (T_{range} \text{abs}(t_{exp} - t_{p\_i}))/T_{range}.$$

In the median parameter expression, $F_{tm}$ represents the closeness to median parameter. The remaining parameters are described above. The scaled left slope parameter may be represented by a scaled left slope parameter expression:

$$F_{sl} = Slope_{i\_left}/Slope_{max}.$$

In the scaled left slope parameter expression, $F_{sl}$ represents the scaled left slope parameter. The remaining parameters are described above. The scaled right slope parameter may be represented by a scaled right slope parameter expression:

$$F_{sr} = Slope_{i\_right}/Slope_{max}.$$

In the scaled right slope parameter expression, $F_{sr}$ represents the scaled right slope parameter. The remaining parameters are described above.

In these and other embodiments, the linear scoring function may be represented by a linear scoring function expression:

$$\text{Score}_{p\_i} = c_1 F_{hm} + c_2 F_{hl} + c_3 F_{hr} + c_4 F_{rm} + c_5 F_{sl} + c_6 F_{sr}; \text{ in which:}$$

in the linear scoring function expression, $c_1$-$c_6$ are constants that may be optimized according to the process of FIG. 2 and methods described elsewhere in the present disclosure. The parameter $\text{Score}_{p\_i}$ represents a candidate peak score. The peak selection module 314 may be configured to select the peak with the highest score that is calculated according to the scoring function. The selected peak may be a real peak. The peaks 304 may be output by the peak selection module 314.

The usage of the peaks 304 may depend on what physiological property is being measured. For ECG and PPG, the peaks 304 represent an effective measurement of the interval between heart beats. A stream of inter-beat intervals may be used to compute a heart rate. Given an average inter-peak interval of T milliseconds, the heart rate is 60000/T, as measured in beats per minute and a heart rate variability, which may be calculated using one or more heart rate variability algorithms.

Figure 6:
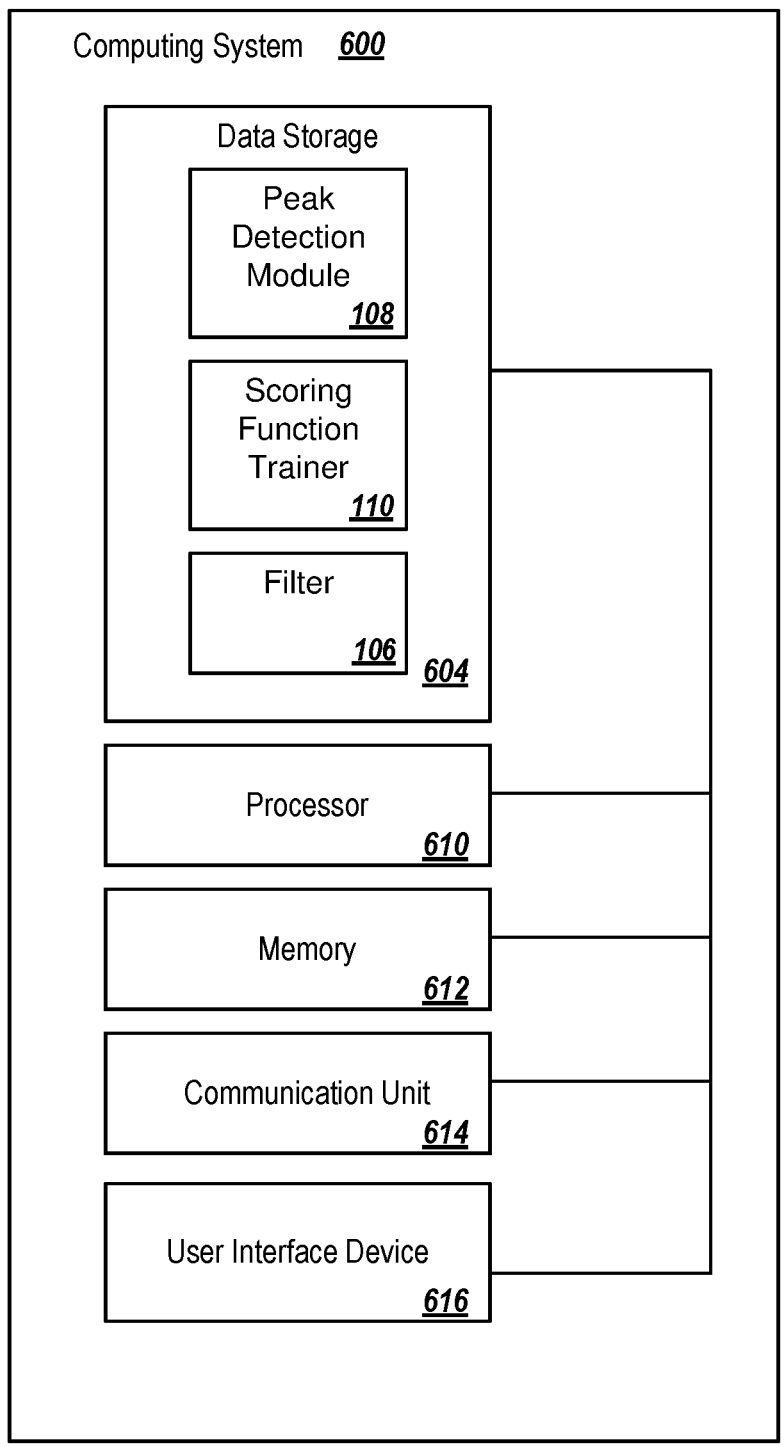
FIG. 6 is a block diagram of an example computing system that may be configured for implementation of peak detection in digital signals derived from a cyclic biological process.

FIG. 6 is a block diagram of an example computing system 600 that may be configured for implementation of peak detection in digital signals derived from a cyclic biological process according to at least one embodiment of the present disclosure. Examples of the computing system 600 may include the mobile device 156 and/or the source 104. The computing system 600 may be implemented in the environments 100A and 100B of FIGS. 1A and 1B, for instance. The computing system 600 may include one or more processors 610, a memory 612, a communication unit 614, a user interface device 616, and a data storage 604 that includes the peak detection module 108, the scoring function trainer 110, and the filter 106 (collectively, modules 106/108/110).

The processor 610 may include any suitable special-purpose or general-purpose computer, computing entity, or processing device including various computer hardware or software modules and may be configured to execute instructions stored on any applicable computer-readable storage media. For example, the processor 610 may include a microprocessor, a microcontroller, a digital signal processor (DSP), an ASIC, an FPGA, or any other digital or analog circuitry configured to interpret and/or to execute program instructions and/or to process data.

Although illustrated as a single processor in FIG. 6, the processor 610 may more generally include any number of processors configured to perform individually or collectively any number of operations described in the present disclosure. Additionally, one or more of the processors 610 may be present on one or more different electronic devices or computing systems. In some embodiments, the processor 610 may interpret and/or execute program instructions and/or process data stored in the memory 612, the data storage 604, or the memory 612 and the data storage 604. In some embodiments, the processor 610 may fetch program instructions from the data storage 604 and load the program instructions in the memory 612. After the program instructions are loaded into the memory 612, the processor 610 may execute the program instructions.

The memory 612 and the data storage 604 may include computer-readable storage media for carrying or having computer-executable instructions or data structures stored thereon. Such computer-readable storage media may include any available media that may be accessed by a general-purpose or special-purpose computer, such as the processor 610. By way of example, and not limitation, such computer-readable storage media may include tangible or non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and that may be accessed by a general-purpose or special-purpose computer. Combinations of the above may also be included within the scope of computer-readable storage media. Computer-executable instructions may include, for example, instructions and data configured to cause the processor 610 to perform a certain operation or group of operations.

The communication unit 614 may include one or more pieces of hardware configured to receive and send communications. In some embodiments, the communication unit 614 may include one or more of an antenna, a wired port, and modulation/demodulation hardware, among other communication hardware devices. In particular, the communication unit 614 may be configured to receive a communication from outside the computing system 600 and to present the communication to the processor 610 or to send a communication from the processor 610 to another device or network.

The user interface device 616 may include one or more pieces of hardware configured to receive input from and/or provide output to a user. In some embodiments, the user interface device 616 may include one or more of a speaker, a microphone, a display, a keyboard, a touch screen, or a holographic projection, among other hardware devices.

The modules 106/108/110 may include program instructions stored in the data storage 604. The processor 610 may be configured to load the modules 106/108/110 into the memory 612 and execute the modules 106/108/110. Alternatively, the processor 610 may execute the modules 106/108/110 line-by-line from the data storage 604 without loading them into the memory 612. When executing the modules 106/108/110, the processor 610 may be configured to perform an unexplored branch search as described elsewhere in this disclosure.

Modifications, additions, or omissions may be made to the computing system 600 without departing from the scope of the present disclosure. For example, in some embodiments, the computing system 600 may not include the user interface device 616. In some embodiments, the different components of the computing system 600 may be physically separate and may be communicatively coupled via any suitable mechanism. For example, the data storage 604 may be part of a storage device that is separate from a server, which includes the processor 610, the memory 612, and the communication unit 614, that is communicatively coupled to the storage device. The embodiments described herein may include the use of a special-purpose or general-purpose computer including various computer hardware or software modules, as discussed in greater detail below.

Figure 7A:
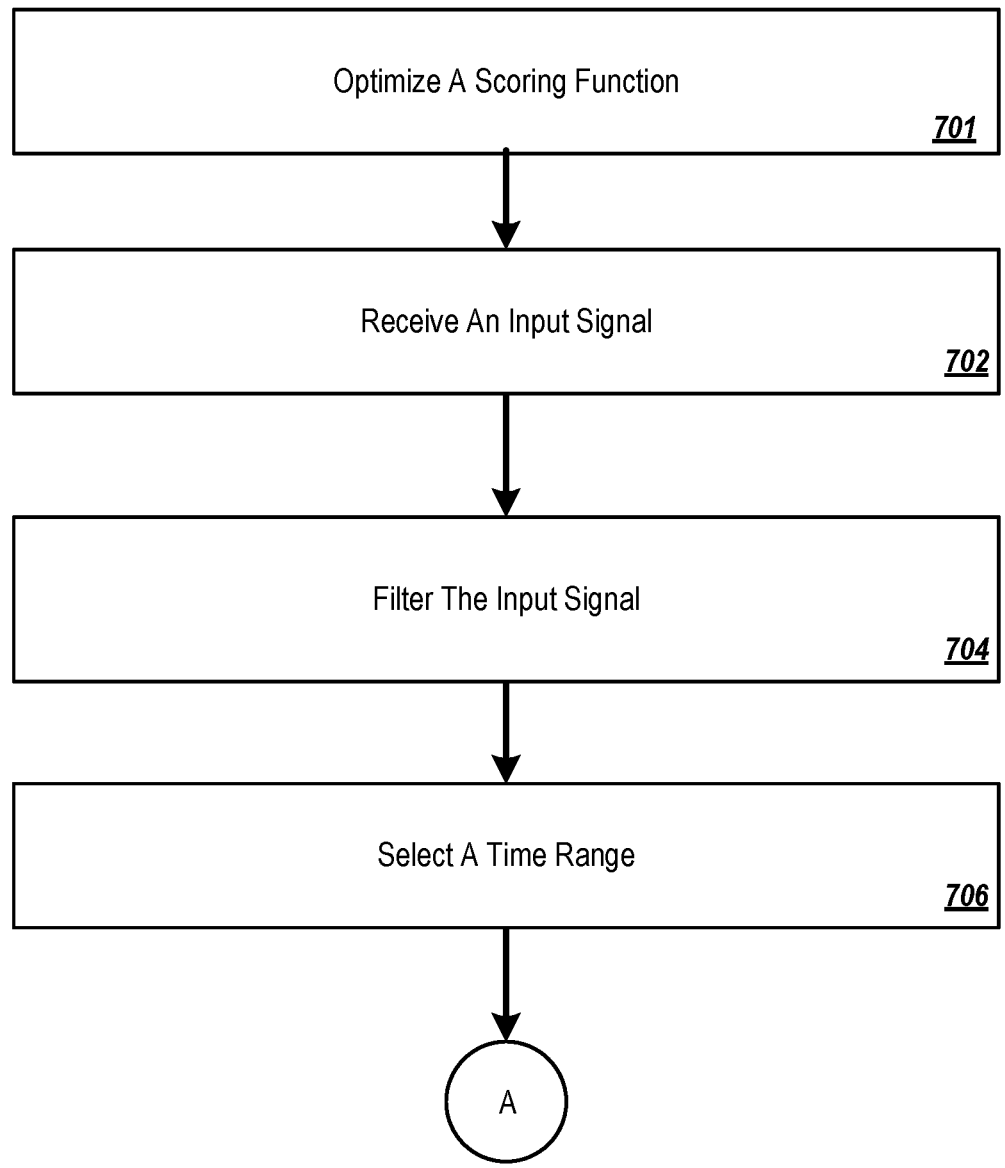
FIGS. 7A and 7B are a flow chart of an example method of peak detection in digital signals derived from a cyclic biological process.
Figure 7B:
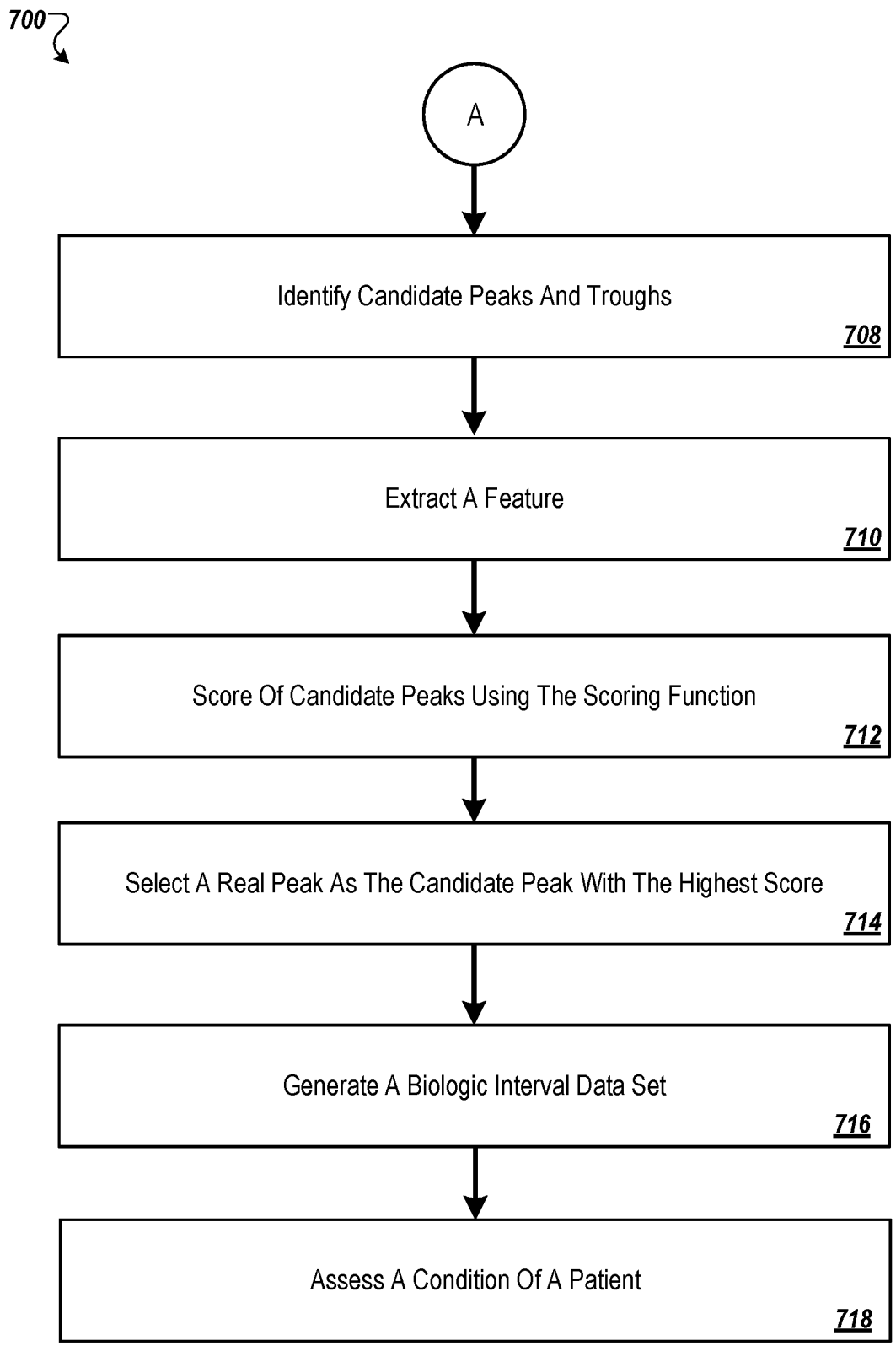

FIGS. 7A and 7B are a flow chart of an example method 700 of peak detection in digital signals derived from a cyclic biological process. Although illustrated as discrete blocks, various blocks in FIGS. 7A and 7B may be divided into additional blocks, combined into fewer blocks, or eliminated, depending on the desired implementation.

The method 700 may begin at block 701 in which a scoring function may be optimized. The scoring function may be optimized using training signals that include one or more known peaks and one or more known features. For example, the scoring function may be optimized using a machine learning technique. The machine learning technique may include, for example a linear regression technique, support vector machines, logistic regression, or Naïve Bayes.

At block 702 an input signal may be received. The input signal may include a digital signal derived from a cyclic biological process. The input signal may be measured from a mobile sensor. The cyclic biological process may include a heart rate or a heart rate variability. At block 704, the input signal may be filtered. The input signal may be filtered using a bandpass filter. The input signal may be filtered to remove low frequency noise and high frequency noise. At block 706, a time range may be selected. The time range of the input signal based on underlying physiological properties of a source. Some examples of the source may include an ECG or a PPG.

Referring to FIG. 7B, at block 708, two or more candidate peaks and two or more troughs may be identified. The candidate peaks and the troughs may be identified within the selected time range. At block 710, a feature may be extracted. The feature may describe properties of the candidate peaks and/or the candidate troughs. Some examples of the feature may include a length of time over which candidate peaks are considered, $T_{range}$; a minimum sample value over the time range, $y_{min}$; a maximum sample value over the time range, $y_{max}$; a sample value for a peak, $y_{p\_i}$, that is indexed by an indexing variable i; a timestamp for the peak, $t_{p\_i}$, that is indexed by the indexing variable i; a sample value, $y_{t\_left}$, for the trough preceding the peak, $y_{p\_i}$, that is indexed by the indexing variable i; a timestamp, $t_{p\_left}$, for the trough preceding the peak, $y_{p\_i}$, that is indexed by the indexing variable i; a sample value, $y_{t\_right}$, for the trough following the peak, $y_{p\_i}$, that is indexed by the indexing variable i; a timestamp, $t_{p\_right}$, for the trough following the peak, $y_{p\_i}$, that is indexed by the indexing variable i; a left slope, $Slope_{i\_left}$, that is equal to $(y_{p\_i}-y_{t\_left})/(t_{p\_i}-t_{t\_left})$; a right slope, $Slope_{i\_right}$, that is equal to $(y_{right}-y_{p\_i})/(t_{right}-t_{p\_i})$; a maximum slope, $Slope_{max}$, and a timestamp of the expected location of the peak, $t_{exp}$.

In some embodiments, the maximum slope may be found for all peaks (p_i) according to an expression $Max_i(Max(Slope_{i\_left}, Slope_{i\_right}))$ in which Max represents a maximizing function. Additionally, in these and other embodiments, the timestamp of the expected location of the peak may be computed by finding a median of a particular number of immediately preceding computed peak intervals and adding the median to the last peak's timestamp.

At block 712, candidate peaks may be scored using the scoring function. The scoring function may be a linear function. The linear function may include a set of constants and a set of parameters of the input signal. In some embodiments, the set of parameters may include a height above minimum parameter, a left height parameter, a right height parameter, a closeness to median parameter, a scaled left slope parameter, a scaled right slope parameter, other parameters, or some combination thereof. The height above minimum parameter, the left height parameter, the right height parameter, the closeness to median parameter, the scaled left slope parameter, and the scaled right slope parameter may be represented by expressions described with reference to FIGS. 3 and 4.

Additionally, in some embodiments, the linear scoring function may be represented by a linear scoring function expression:

$$Score_{p\_i}=c_1F_{hm}+c_2F_{hl}+c_3F_{hr}+c_4F_{tm}+c_5F_{sl}+c_6F_{sr}.$$

In the linear scoring function expression, $c_1$-$c_6$ are constants that are optimized in block 701. The parameter $Score_{p\_i}$ represents a candidate peak score. At block 714, a real peak may be selected from the two or more candidate peaks as the candidate peak with the highest score calculated according to the scoring function. At block 716, a biologic interval data set may be generated. The biologic interval data set may include the selected peak and at least one other peak. The biologic interval data set may be representative of health markers related to a condition of the patient. An example of the biologic interval may include a heart rate or a heart rate variability. At block 718, the condition of the patient may be assessed. The condition may be assessed based on the biologic interval data set.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Figure 8:
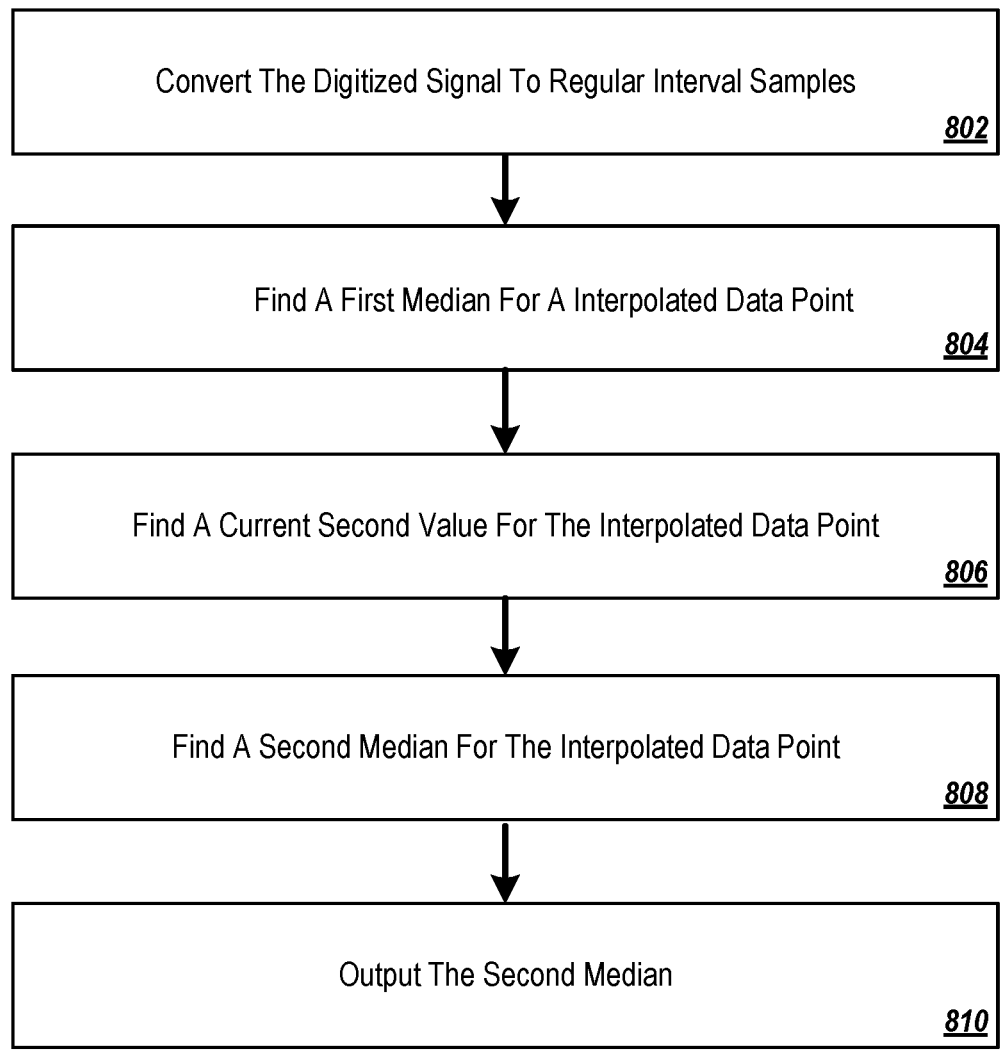
FIG. 8 is a flow chart of an example method of filtering digital signals derived from a cyclic biological process.

FIG. 8 is a flow chart of an example method 800 of filtering digital signals derived from a cyclic biological process according to at least one embodiment described in the present disclosure. In some embodiments, the method 800 may be implemented as a part of another method. For instance, the method 800 may be implemented as block 704 of the method 700 described above. Although illustrated as discrete blocks, various blocks in FIG. 8 may be divided into additional blocks, combined into fewer blocks, or eliminated, depending on the desired implementation.

The method 800 may begin at block 802 in which a digitized signal may be converted to regular interval samples. The digitized signal may be converted using linear interpolation. For example, responsive to the digitized signal not being sampled at regular intervals, the digitized signal may be converted to the regular interval samples.

At block 804, a first median may be found for a current interpolated data point. The first median may be found of a first number of preceding interpolated data points including the current interpolated data point. The first number of preceding interpolated data points may be equal to about one hundred preceding interpolated data points in some embodiments. At block 806, a current second value may be found for the interpolated data point. The current second value may be found that may be equal to a difference between the current interpolated data point and the first median.

At block 808, a second median may be found for the interpolated data point. The second median may be found of a second number of preceding second values including the current second median. The second number of preceding second values may be equal to about four preceding second values. At block 810, the second median may be output.

Figure 9:
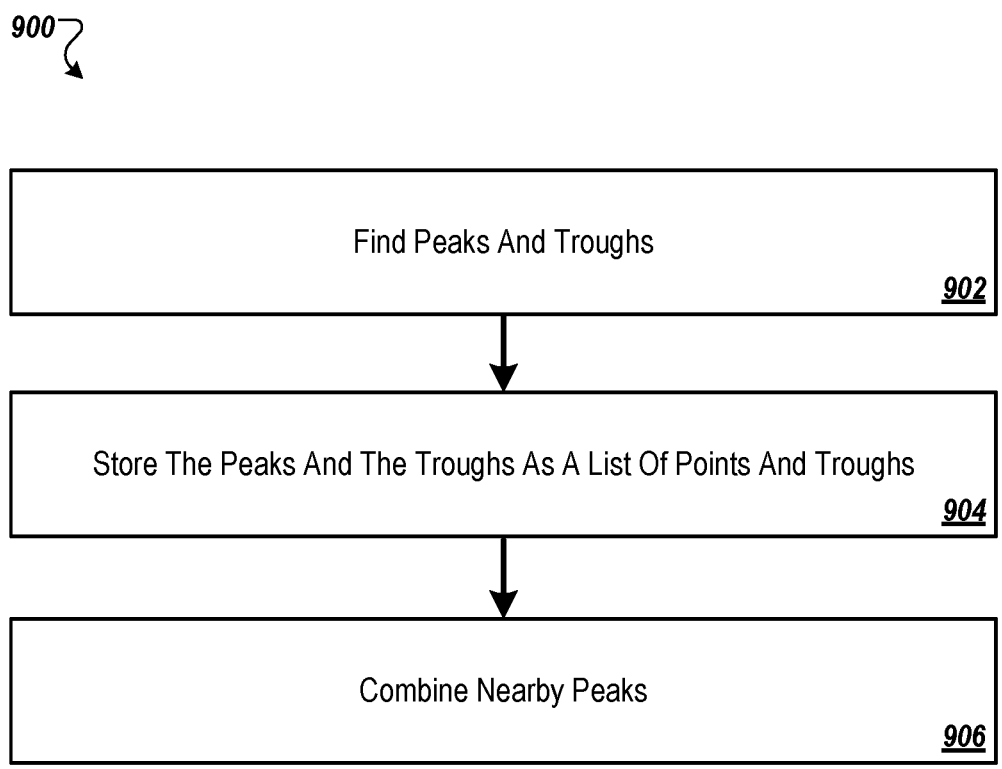
FIG. 9 is a flow chart of an example method of identifying candidate peaks and/or candidate troughs in digital signals derived from a cyclic biological process.

FIG. 9 is a flow chart of an example method 900 of identifying candidate peaks and/or candidate troughs in digital signals derived from a cyclic biological process according to at least one embodiment described in the present disclosure. In some embodiments, the method 900 may be implemented as a part of another method. For instance, the method 900 may be implemented as block 708 of the method 700 described above. Although illustrated as discrete blocks, various blocks in FIG. 9 may be divided into additional blocks, combined into fewer blocks, or eliminated, depending on the desired implementation.

The method 900 may begin at block 902 in which peaks and troughs are found. The peaks and the troughs are found within a time range which may be selected based on underlying physiological properties of a source (e.g., in block 706 of FIG. 7). In some embodiments, the peaks may each include a sequence of one or more samples of the same value in which the sample immediately preceding the sequence has a lower value and the sample immediately following the sequence also has a lower value. Additionally, in some embodiments, the troughs may each include a sequence of one or more samples of the same value in which the sample immediately preceding the sequence has a higher value and the sample immediately following the sequence also has a higher value.

At block 904, the peaks and the troughs may be stored as a list of peaks and troughs. In some embodiments, each point of the list of peaks and troughs may include a timestamp, a sample value, an indication of whether the point is a peak or a trough, other information, or combinations thereof. At block 906, nearby peaks may be combined.

Figure 10A:
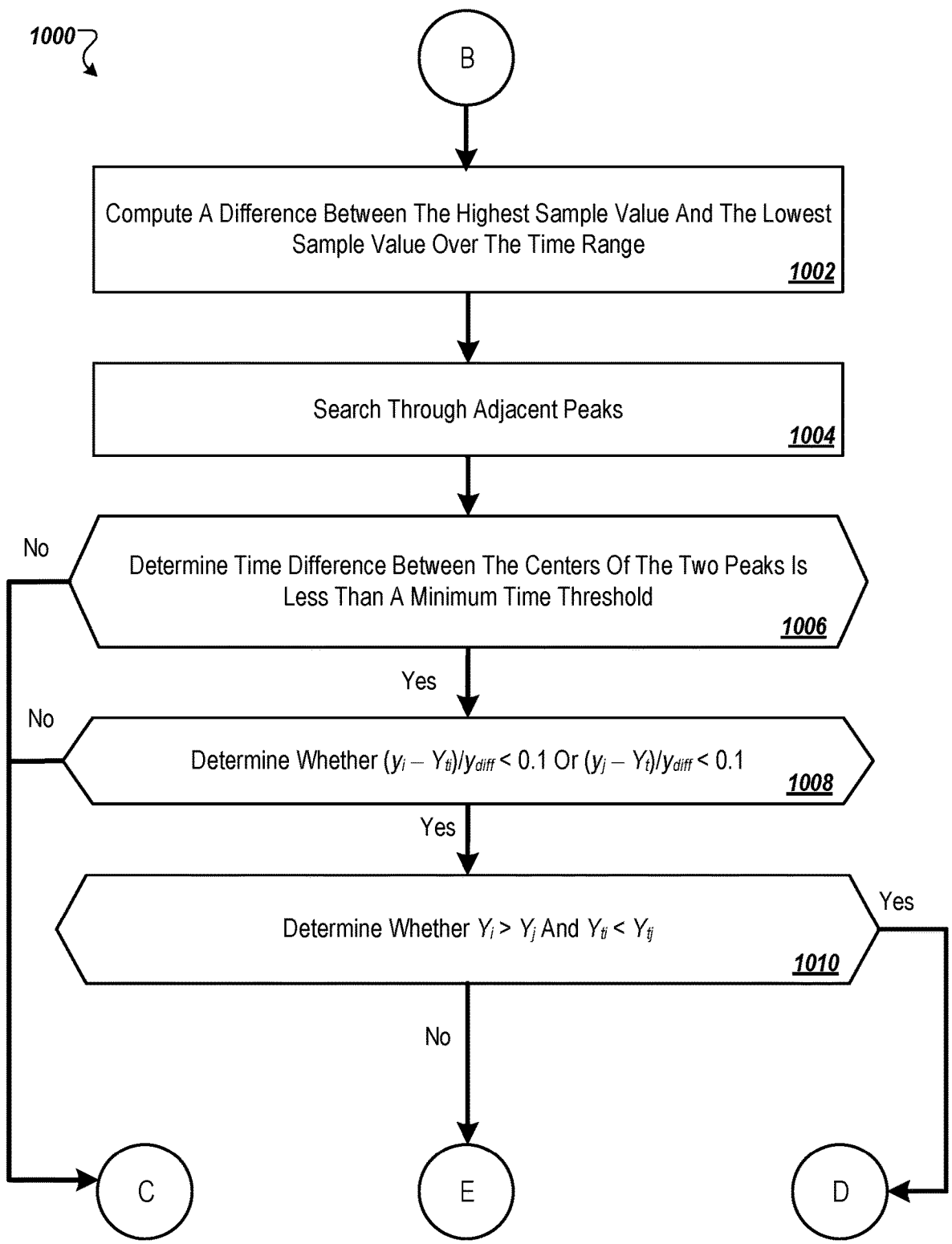
FIGS. 10A and 10B are a flow chart of another example method of combining nearby peaks in digital signals derived from a cyclic biological process, all according to at least one embodiment described in the present disclosure.
Figure 10B:
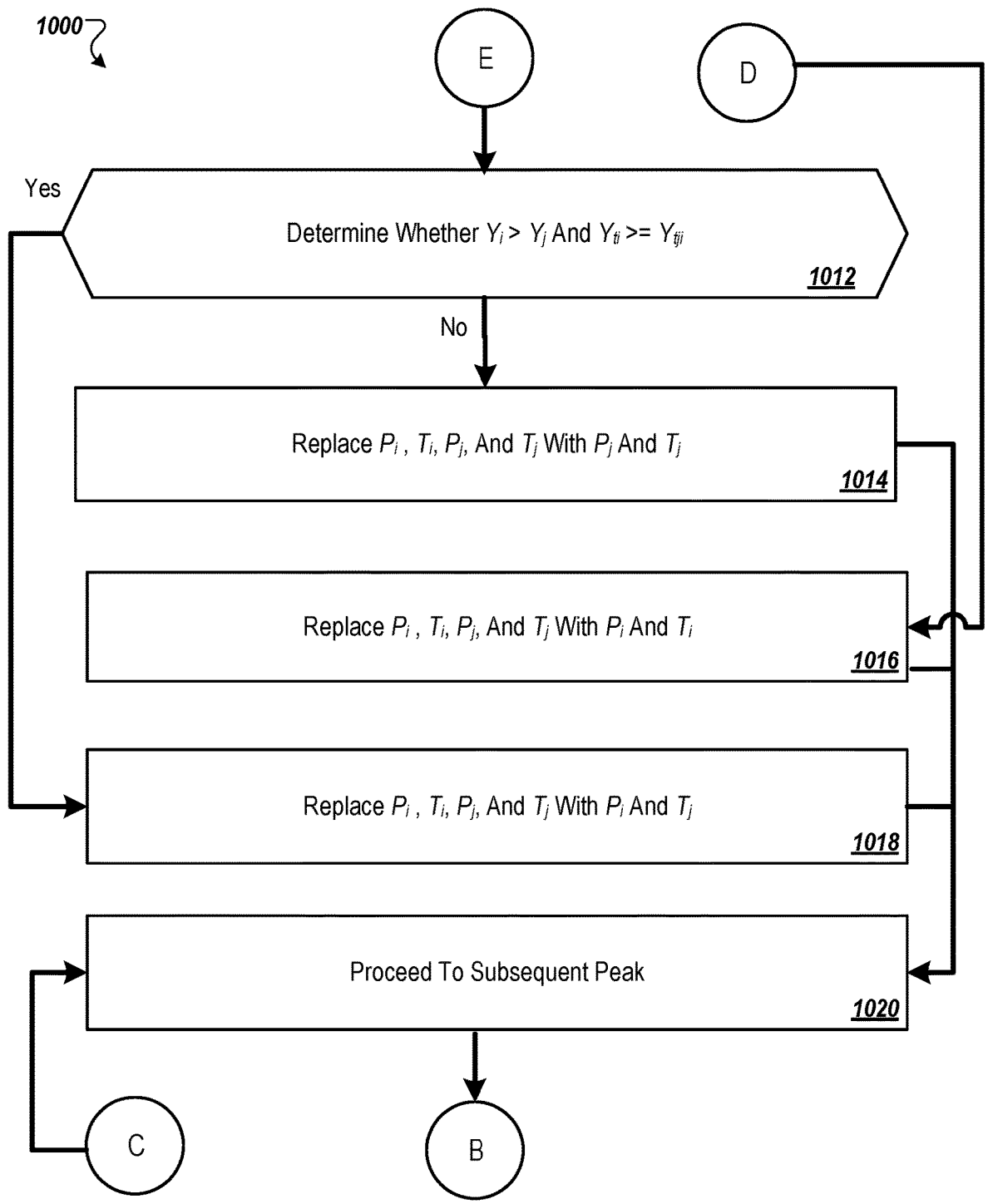

FIGS. 10A and 10B are a flow chart of an example method 1000 of combining nearby peaks in digital signals derived from a cyclic biological process according to at least one embodiment described in the present disclosure. In some embodiments, the method 1000 may be implemented as a part of another method. For instance, the method 1000 may be implemented as block 906 of the method 900 described above. Although illustrated as discrete blocks, various blocks in FIG. 10 may be divided into additional blocks, combined into fewer blocks, or eliminated, depending on the desired implementation.

The method 1000 may begin at block 1002 in which a difference ($y_{diff}$) between the highest sample value and the lowest sample value may be computed. The difference may be computed over a time range that may be selected based on underlying physiological properties of a source of the digital signals. At block 1004, adjacent peaks may be searched. The searched peaks may be combined based on execution of one or more or a combination of blocks 1006, 1008, 1010, 1012, 1014, and 1016. In blocks 1006, 1008, 1010, 1012, 1014, and 1016, parameters and expressions are used instead of corresponding words that are represented by the parameters. For example, in 1006, 1008, 1010, 1012, 1014, and 1016, peaks $p_i$ and $p_j$ represent peaks. The parameter $t_i$ represents a trough between the peaks $p_i$ and $p_j$. The parameter $y_i$ represents the sample value of peak $p_i$. The parameter $y_j$ is the sample value of peak $p_j$. The parameter $y_{ti}$ is the sample value of the trough $t_i$ between the peaks $p_i$ and $p_j$. As described above, the parameter $y_{diff}$ is the difference between the highest sample value and the lowest sample value.

At block 1006, it may be determined whether a time difference between centers of the two peaks $p_i$ and $p_j$ is less than a minimum time threshold. In some embodiment, the minimum time threshold may be about 0.3 seconds. In response to the time difference being less than a minimum time threshold ("Yes" at block 1006), the method 1000 may proceed to block 1008. In response to the time difference being greater than or equal to the minimum time threshold ("No" at block 1006), the method 1000 may proceed to block 1020.

At block 1008, it may be determined whether $(y_i-y_{ti})/y_{diff}<0.1$ or 0.1. In response to $(y_i-y_{ti})/y_{diff}<0.1$ or $(y_j-y_t)/y_{diff}<0.1$ ("Yes" at block 1008), the method 1000 may proceed to block 1010. In response to $(y_i-y_{ti})/y_{diff}>=0.1$ and $(y_j-y_t)/y_{diff}>=0.1$ ("No" at block 1008), the method 1000 may proceed to block 1020.

At block 1010, it may be determined whether $y_i>y_j$ and $y_{ti}<y_{tj}$. In response to $y_i>y_j$ and $y_{ti}<y_{tj}$ ("Yes" at block 1010), the method 1000 may proceed to block 1016. At block 1016 of FIG. 10B, $p_i$, $t_i$, $p_j$, and $t_j$ may be replaced by $p_i$ and $t_j$ in a list of peaks and troughs. In response to $y_i<=y_j$ or $y_{ti}>=y_{tj}$ ("No" at block 1010), the method 1000 may proceed to block 1012.

At block 1012, it may be determined whether $y_i>y_j$ and $y_{ti}>=y_{tj}$. In response to $y_i>y_j$ and $y_{ti}>=y_{tj}$ ("Yes" at block 1012), the method 1000 may proceed to block 1018. At block 1018, $p_i$, $t_i$, $p_j$, and $t_j$ may be replaced by $p_j$ and $t_j$ in the list of peaks and troughs. In response to $y_i<=y_j$ or $y_{ti}<y_{tj}$ ("No" at block 1012), the method 1000 may proceed to block 1014. At block 1014, $p_i$, $t_i$, $p_j$, and $t_j$ may be replaced by $p_i$ and $t_i$ in the list of peaks and troughs. From each of blocks 1014, 1016, and 1018, the method 1000 may proceed to block 1020. At block 1020, the method 1000 may proceed to a subsequent peak. Following block 1020, the method 1000 may proceed through one or more or a combination of the blocks 1002, 1004, 1006, 1008, 1010, 1012, 1014, 1016, and 1018 for the subsequent peak.

The methods 700, 800, 900, and 1000 may be performed in an environment such as the environments 100A and 100B of FIGS. 1A and 1B. The methods 700, 800, 900, and 1000 may be programmably performed in some embodiments by the peak detection module 108 described with reference to FIGS. 1-3 or the computing system 600 of FIG. 6. In some embodiments, a computing system (e.g., 600) including the peak detection module 108 may include or may be communicatively coupled to a non-transitory computer-readable medium (e.g., the memory 612 of FIG. 6) having stored thereon programming code or instructions that are executable by one or more processors (such as the processor 610 of FIG. 6) to cause a computing system to perform or control performance of the methods 700, 800, 900, 1000 or some combination thereof. Additionally or alternatively, a computing system (e.g., 600) including the peak detection module 108 may include the processor 610 described elsewhere in this disclosure that is configured to execute computer instructions to cause the computing system to perform or control performance of the methods 700, 800, 900, 1000 or some combination thereof.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. In these and other embodiments, the term "non-transitory" as explained herein should be construed to exclude only those types of transitory media that were found to fall outside the scope of patentable subject matter in the Federal Circuit decision of *In re Nuijten,* 500 F.3d 1346 (Fed. Cir. 2007). Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads).

While some of the system and methods described herein are generally described as being implemented in software (stored on and/or executed by general-purpose hardware), specific hardware implementations or a combination of software and specific hardware implementations are also possible and contemplated. In this description, a "computing entity" may be any computing system as previously defined herein, or any module or combination of modulates running on a computing system.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A method of real peak detection, the method comprising:
   receiving an input signal, the input signal including a digital signal derived from a cyclic biological process of a patient that is measured by a mobile sensor;
   filtering, using a bandpass filter, the input signal to remove low frequency noise and high frequency noise;
   selecting a time range of the input signal based on underlying physiological properties of a source;
   identifying two or more candidate peaks and two or more troughs within the selected time range;
   extracting from the input signal a feature that describes a property of the two or more candidate peaks;
   scoring the two or more candidate peaks using a scoring function;
   selecting a real peak from the two or more candidate peaks as the candidate peak with the highest score calculated according to the scoring function;
   generating a biologic interval data set that includes the real peak and at least one other peak, the biologic interval data set being representative of health markers related to a condition of the patient; and
   based on the biologic interval data set, assessing the condition of the patient, wherein the scoring function is a linear combination which combines and weighs multiple features of the digital signal into a single value.

2. The method of claim 1, wherein the filtering includes:
responsive to the digitized signal not being sampled at regular intervals, converting the digitized signal to regular interval samples using linear interpolation; and
for a current interpolated data point:
finding a first median of a first number of preceding interpolated data points including the current interpolated data point;
finding a current second value that is equal to a difference between the current interpolated data point and the first median;
finding a second median of a second number of preceding second values including the current second median; and
outputting the second median.

3. The method of claim 2, wherein:
the first number of preceding interpolated data points is equal to about one hundred preceding interpolated data points; and
the second number of preceding second values is equal to about four preceding second values.

4. The method of claim 1, wherein the identifying the two or more candidate peaks and the two or more troughs includes:
finding peaks and troughs within the selected time range, wherein:
the peaks each include a sequence of one or more samples of the same value in which the sample immediately preceding the sequence has a lower value and the sample immediately following the sequence also has a lower value, and
the troughs each include a sequence of one or more samples of the same value in which the sample immediately preceding the sequence has a higher value and the sample immediately following the sequence also has a higher value;
storing the peaks and the troughs as a list of peaks and troughs, wherein each point of the list of peaks and troughs has a timestamp, a sample value, and an indication of whether the point is a peak or a trough; and
combining nearby peaks.

5. The method of claim 4, wherein the combining the nearby peaks includes:
computing a difference ($y_{diff}$) between the highest sample value and the lowest sample value over the time range;
searching through adjacent peaks;
selecting peaks $p_i$ and $p_j$ for combining if:
the time difference between centers of the two peaks is less than a minimum time threshold, $T_{min}$, and
$(y_i-y_{ti})/y_{diff}<0.1$ or $(y_j-y_t)/y_{diff}<0.1$, in which:
$y_i$ is the sample value of peak $p_i$,
$y_j$ is the sample value of peak $p_j$, and
$y_d$ is the sample value of the trough $t_i$ between peaks $p_i$ and $p_j$; and
replacing $p_i$, $t_i$, $p_j$, and $t_j$ in the list of peaks and troughs, with:
$p_i$ and $t_i$ if $y_i>y_j$ and $y_{ti}<y_{tj}$;
$p_i$ and $t_j$ if $y_i>y_j$ and $y_{ti}>=y_{tj}$; and
$p_j$ and $t_j$ otherwise.

6. The method of claim 1, wherein the feature includes:
a length of time over which candidate peaks are considered, $T_{range}$;
a minimum sample value over the time range, $y_{min}$;
a maximum sample value over the time range, $y_{max}$;
a timestamp of the expected location of a peak, $t_{exp}$;
a sample value for a peak, $y_{p\_i}$, that is indexed by an indexing variable i;
a timestamp for a peak, $t_{p\_i}$, that is indexed by the indexing variable i;
a sample value, $y_{t\_left}$, for the trough preceding a peak, $y_{p\_i}$, that is indexed by the indexing variable i;
a timestamp, $t_{p\_left}$, for the trough preceding a peak, $y_{p\_i}$, that is indexed by the indexing variable i;
a sample value, $y_{t\_right}$, for the trough following a peak, $y_{p\_i}$, that is indexed by the indexing variable i;
a timestamp, $t_{p\_right}$, for the trough following a peak, $y_{p\_i}$, that is indexed by the indexing variable i;
a left slope, $Slope_{i\_left}$, that is equal to $(y_{p\_i}-y_{t\_left})/(t_{p\_i}-t_{t\_left})$;
a right slope, $Slope_{i\_right}$, that is equal to $(y_{right}-y_{p\_i})/(t_{right}-t_{p\_i})$; and
a maximum slope, $Slope_{max}$, that is found for all peaks (p_i) according to an expression:
$Max_i(Max(Slope_{i\_left}, Slope_{i\_right}))$ in which Max represents a maximizing function.

7. The method of claim 6, wherein the timestamp of the expected location of a peak is computed by finding a median of a particular number of immediately preceding computed peak intervals and adding the median to a timestamp of an immediately preceding peak.

8. The method of claim 6, wherein:
the scoring function is a linear function of a height above minimum parameter, a left height parameter, a right height parameter, a closeness to median parameter, a scaled left slope parameter, and a scaled right slope parameter; and
the height above minimum parameter is represented by an expression:
$F_{hm}=(y_{p\_1}-y_{min})/(y_{max}-y_{min})$ in which $F_{hm}$ represents height above minimum parameter;
the left height parameter is represented by an expression:
$F_{hl}=(y_{p\_i}-y_{t\_left})/(y_{max}-y_{min})$ in which $F_{hl}$ represents the left height parameter;
the right height parameter is represented by an expression:
$F_{hr}=(y_{i\_p}-y_{t\_right})/(y_{max}-y_{min})$ in which $F_{hr}$ represents the right height parameter;
the closeness to median parameter is represented by an expression:
$F_{tm}=(T_{range}-abs(t_{exp}-t_{p\_i}))/T_{range}$ in which $F_{tm}$ represents the closeness to median parameter;
the scaled left slope parameter is represented by an expression:
$F_{sl}=Slope_{i\_left}/Slope_{max}$ in which $F_{sl}$ represents the scaled left slope parameter; and
the scaled right slope parameter is represented by an expression:
$F_{sr}=Slope_{i\_right}/Slope_{max}$ in which $F_{sr}$ represents the scaled right slope parameter.

9. The method of claim 8, wherein the linear scoring function is represented by an expression:

$Score_{p\_i}=c_1F_{hm}+c_2F_{hl}+c_3F_{hr}+c_4F_{tm}+c_5F_{sl}+c_6F_{sr}$; in which:

$c_1$-$c_6$ are constants; and
$Score_{p\_i}$ represents a candidate peak score.

10. The method of claim 9, further comprising optimizing the scoring function using training signals that include one or more known peaks and one or more known features, wherein:

the constants of the linear scoring function are optimized by a machine learning technique that includes:
a linear regression technique;
a support vector machine;
Logistic Regression; or
Naïve Bayes;
the cyclic biological process includes a heartbeat interval or a heart rate variability; and
the source includes an Echocardiogram (ECG) or a Photoplethysmogram (PPG).

11. A non-transitory computer-readable medium having encoded therein programming code executable by one or more processors to perform or control performance of operations comprising:
receiving an input signal, the input signal including a digital signal derived from a cyclic biological process of a patient that is measured by a mobile sensor;
filtering, using a bandpass filter, the input signal to remove low frequency noise and high frequency noise;
selecting a time range of the input signal based on underlying physiological properties of a source;
identifying two or more candidate peaks and two or more troughs within the selected time range;
extracting from the input signal a feature that describes a property of the two or more candidate peaks;
scoring the two or more candidate peaks using a scoring function;
selecting a real peak from the two or more candidate peaks as the candidate peak with the highest score calculated according to the scoring function;
generating a biologic interval data set that includes the real peak and at least one other peak, the biologic interval data set being representative of health markers related to a condition of the patient; and
based on the biologic interval data set, assessing the condition of the patient,
wherein the scoring function is a linear combination which combines and weighs multiple features of the digital signal into a single value.

12. The non-transitory computer-readable medium of claim 11, wherein the filtering includes:
responsive to the digitized signal not being sampled at regular intervals, converting the digitized signal to regular interval samples using linear interpolation; and
for a current interpolated data point:
finding a first median of a first number of preceding interpolated data points including the current interpolated data point;
finding a current second value that is equal to a difference between the current interpolated data point and the first median;
finding a second median of a second number of preceding second values including the current second median; and
outputting the second median.

13. The non-transitory computer-readable medium of claim 12, wherein:
the first number of preceding interpolated data points is equal to about one hundred preceding interpolated data points; and
the second number of preceding second values is equal to about four preceding second values.

14. The non-transitory computer-readable medium of claim 11, wherein the identifying the two or more candidate peaks and the two or more troughs includes:
finding peaks and troughs within the selected time range, wherein:
the peaks each include a sequence of one or more samples of a same value in which the sample immediately preceding the sequence has a lower value and the sample immediately following the sequence also has a lower value, and
the troughs each include a sequence of one or more samples of the same value in which the sample immediately preceding the sequence has a higher value and the sample immediately following the sequence also has a higher value;
storing the peaks and the troughs as a list of peaks and troughs, wherein each point of the list of peaks and troughs has a timestamp, a sample value, and an indication of whether the point is a peak or a trough; and
combining nearby peaks.

15. The non-transitory computer-readable medium of claim 14, wherein the combining the nearby peaks includes:
computing a difference ($y_{diff}$) between a highest sample value and a lowest sample value over the time range;
searching through adjacent peaks;
selecting peaks $p_i$ and $p_j$ for combining if:
the time difference between centers of the two peaks is less than a minimum time threshold, $T_{min}$, and
$(y_i-y_{ti})/y_{diff}<0.1$ or $(y_j-y_t)/y_{diff}<0.1$, in which:
$y_i$ is the sample value of peak $p_i$,
$y_j$ is the sample value of peak $p_j$, and
$y_d$ is the sample value of the trough $t_i$ between peaks $p_i$ and $p_j$; and
replacing $p_i$, $t_i$, $p_j$, and $t_j$ in the list of peaks and troughs, with:
$p_i$ and $t_i$ if $y_i>y_j$ and $y_{ti}<y_{tj}$;
$p_i$ and $t_j$ if $y_i>y_j$ and $y_{ti}>=y_{tj}$; and
$p_j$ and $t_j$ otherwise.

16. The non-transitory computer-readable medium of claim 11, the feature includes:
a length of time over which candidate peaks are considered, $T_{range}$;
a minimum sample value over the time range, $y_{min}$;
a maximum sample value over the time range, $y_{max}$;
a timestamp of the expected location of the peak, $t_{exp}$;
a sample value for a peak, $y_{p\_i}$, that is indexed by an indexing variable i;
a timestamp for the peak, $t_{p\_i}$, that is indexed by the indexing variable i;
a sample value, $y_{t\_left}$, for the trough preceding the peak, $y_{p\_i}$, that is indexed by the indexing variable i;
a timestamp, $t_{p\_left}$, for the trough preceding the peak, $y_{p\_i}$, that is indexed by the indexing variable i;
a sample value, $y_{t\_right}$, for the trough following the peak, $y_{p\_i}$, that is indexed by the indexing variable i;
a timestamp, $t_{p\_right}$, for the trough following the peak, $y_{p\_i}$, that is indexed by the indexing variable i;
a left slope, $Slope_{i\_left}$, that is equal to $(y_{p\_i}-y_{t\_left})/(t_{p\_i}-t_{t\_left})$;
a right slope, $Slope_{i\_right}$, that is equal to $(y_{right}-y_{p\_i})/(t_{right}-t_{p\_i})$;
a maximum slope, $Slope_{max}$, that is found for all peaks (p_i) according to an expression:
$Max_i(Max(Slope_{i\_left}, Slope_{i\_right}))$ in which Max represents a maximizing function.

17. The non-transitory computer-readable medium of claim 16, wherein the timestamp of the expected location of the peak is computed by finding a median of a particular number of immediately preceding computed peak intervals and adding the median to a timestamp of an immediately preceding peak.

18. The non-transitory computer-readable medium of claim 16, wherein:
- the scoring function is a linear function of a height above minimum parameter, a left height parameter, a right height parameter, a closeness to median parameter, a scaled left slope parameter, and a scaled right slope parameter; and
- the height above the minimum parameter is represented by an expression:
  $F_{hm}=(y_{p\_i}-y_{min})/(y_{max}-y_{min})$ in which $F_{hm}$ represents the height above minimum parameter;
- the left height parameter is represented by an expression:
  $F_{hl}=(y_{p\_i}-y_{t\_left})/(y_{max}-y_{min})$ in which $F_{hl}$ represents the left height parameter;
- the right height parameter is represented by an expression:
  $F_{hr}=(y_{p\_i}-y_{t\_right})/(y_{max}-y_{min})$ in which $F_{hr}$ represents the right height parameter;
- the closeness to median parameter is represented by an expression:
  $F_{tm}=(T_{range}-abs(t_{exp}-t_{p\_i}))/T_{range}$ in which $F_{tm}$ represents the closeness to median parameter;
- the scaled left slope parameter is represented by an expression:
  $F_{sl}=Slope_{i\_left}/Slope_{max}$ in which $F_{sl}$ represents the scaled left slope parameter; and
- the scaled right slope parameter is represented by an expression:
  $F_{sr}=Slope_{i\_right}/Slope_{max}$ in which $F_{sr}$ represents the scaled right slope parameter.

19. The non-transitory computer-readable medium of claim 18, wherein the linear scoring function is represented by an expression:

$$Score_{p\_i}=c_1 F_{hm}+c_2 F_{hl}+c_3 F_{hr}+c_4 F_{tm}+c_5 F_{sl}+c_6 F_{sr};$$ in which:
- $c_1$-$c_6$ are constants; and
- $Score_{p\_i}$ represents a candidate peak score.

20. The non-transitory computer-readable medium of claim 18, wherein:
- the operations further comprise optimizing a scoring function using training signals that include one or more known peaks and one or more known features,
- the constants of the linear scoring function are optimized by a machine learning technique that includes:
- a linear regression technique;
- a support vector machine;
- Logistic Regression; or
- Naïve Bayes;
- the cyclic biological process includes a heartbeat interval or a heart rate variability; and
- the source includes an Echocardiogram (ECG) or a Photoplethysmogram (PPG).

* * * * *